United States Patent
Lee

(10) Patent No.: US 11,786,494 B2
(45) Date of Patent: *Oct. 17, 2023

(54) METHODS OF MODULATION OF BRANCHED CHAIN ACIDS AND USES THEREOF

(71) Applicant: Baylor College of Medicine, Houston, TX (US)

(72) Inventor: Brendan Lee, Houston, TX (US)

(73) Assignee: Baylor College of Medicine, Houston, TX (US)

(*) Notice: Subject to any disclaimer, the term of this patent is extended or adjusted under 35 U.S.C. 154(b) by 30 days.

This patent is subject to a terminal disclaimer.

(21) Appl. No.: 16/740,131

(22) Filed: Jan. 10, 2020

(65) Prior Publication Data

US 2020/0147016 A1   May 14, 2020

Related U.S. Application Data

(63) Continuation of application No. 16/134,558, filed on Sep. 18, 2018, now abandoned, which is a continuation of application No. 15/653,155, filed on Jul. 18, 2017, now Pat. No. 10,092,532, which is a continuation of application No. 14/745,205, filed on Jun. 19, 2015, now Pat. No. 9,737,499, which is a continuation of application No. 13/386,549, filed as
(Continued)

(51) Int. Cl.
*A61K 31/192* (2006.01)

(52) U.S. Cl.
CPC ................ *A61K 31/192* (2013.01)

(58) Field of Classification Search
CPC ................ A61K 31/192; A61P 3/00
See application file for complete search history.

(56) References Cited

U.S. PATENT DOCUMENTS

| | | | |
|---|---|---|---|
| 5,434,166 A | 7/1995 | Glasebrook | |
| 6,362,226 B2* | 3/2002 | Phillips, III | A61K 31/485 514/568 |
| 6,503,530 B1 | 1/2003 | Kang et al. | |

(Continued)

FOREIGN PATENT DOCUMENTS

| | | |
|---|---|---|
| WO | 2007005633 A2 | 1/2007 |
| WO | 2008083226 A2 | 7/2008 |

OTHER PUBLICATIONS

Clark-Taylor et al., Medical Hypotheses (2004) 62, 970-975 (Year: 2004).*

(Continued)

*Primary Examiner* — San Ming R Hui
(74) *Attorney, Agent, or Firm* — Norton Rose Fulbright US LLP

(57) ABSTRACT

A method of modulating plasma levels of branched chain amino acids and branched chain alpha-keto acids is disclosed, wherein an ammonia scavenger compound or a salt thereof, for example phenylbutyrate or an even numbered congener thereof or a salt thereof, is administered to an individual in need thereof. In various methods, a decrease in plasma levels of branched chain amino acids and branched chain alpha-keto acids is effected to treat individuals suffering from an inborn error in metabolism of amino acids, such as Maple Syrup Urine Disease, for example.

10 Claims, 8 Drawing Sheets

Related U.S. Application Data application No. PCT/US2010/043240 on Jul. 26, 2010, now Pat. No. 9,078,865.

(60) Provisional application No. 61/228,485, filed on Jul. 24, 2009.

(56) References Cited

U.S. PATENT DOCUMENTS

| | | | | |
|---|---|---|---|---|
| 7,396,659 B2* | 7/2008 | Singh | ............... | A61K 31/472 |
| | | | | 435/25 |
| 2002/0115716 A1* | 8/2002 | Chaturvedi | ............ | A61P 35/00 |
| | | | | 514/529 |
| 2010/0008859 A1 | 1/2010 | Scharschmidt | | |

OTHER PUBLICATIONS

Scaglia et al., Molecular Genetics and Metabolism, 81 (2004) S79-85 (Year: 2004).*
Extended European Search Report dated Apr. 5, 2013, during prosecution of European Patent Application No. 10803013.1-1464 / 2456304 PCT/US2010/043240.
Scaglia et al., "Effect of Alternative Pathway Therapy on Branched Chain Amino Acid Metabolism in Urea Cycle Disorder Patients", Molecular Genetics and Metabolism, Apr. 2004, vol. 81, No. Suppl. 1, pp. S79-S85.
Bunchman et al., "Phenylacetate and Benzoate Clearance in a Hyperammonemic Infant on Sequential Hemodialysis and Hemofiltration", Pediatric Nephrology 200707 DE, vol. 22, No. 7, Jul. 2007, pp. 1062-1065.
Self et al., "Glutamine Synthesis in the Developing Porcine Placenta", Biology of Reproduction 70, 144-1451 (2004).
Funchal et al., "Evidence That the Branched-Chain α-Keto Acids Accumulating in Maple Syrup Urin Diease Induce Morpholigical Alteration and Death in Cultured Astroxytes from Rat Ceberal Cortex", GLIA 48:230-240 (2004).
Funchal et al, "Morphological alterations and induction of oxidative stress in glial cells caused by the branched-chain α-keto acids accumulting in maple syrup urine disease", Neurochemistry International 49 640-650 (2006).
Amaral et al.; "α-Ketoisocaproic acid and leucine provoke mitochondrial bioenergetic dysfunction in rat brain", Science Direct—Brain Research 1324 75-84 (2010).
Darmaun et al., Am. J. Physiol, 1998;274(5):E801-807.
Riazi et al., Am J Physiol Endocrinol Metab, 2004;287:E142-E149.
"Ammo naps—sodium phenylbutyrate. EPAR summary for the public," website of European Medicines Agency (EMEA), located at www.ema.europa.eu/docs/en_GB/document_library/EPAR -_Summary _for_ the _public/human /000219/WC500024 751.pdf, last updated in Dec. 2009.
"Buphenyl (sodium phenylbutyrate) Tablets I Buphenyl (sodium phenylbutyrate) Powder," Patient Package Insert, Ucyclyd Pharma, Inc., Apr. 2009.
Package Leaflet: Information for the User-Ammonaps 940 mg/g granules-sodium phenylbutyrate, website of the electronic Medicines Compendium (eMC), located at www.medicines.org.uk/emc/medicine/24885/PIL/ammonaps%20940%20mg~g%20granules/, pp. 1-5, last approved in Oct. 2010.
"Scientific Discussion," module reflecting the initial scientific discussion for the approval of Ammonpas, updated until Nov. 1, 2001, European Medicines Agency, pp. 1-12, 2005.
Fisher et al., "Molecular phenotypes in cultured maple syrup urine disease cells: Complete E1a eDNA sequence and mRNA and subunit contents of the human branched chain a-keto acid dehydrogenase complex," The Journal of Biological Chemistry, 264(6):3448-3453, 1989.
International Preliminary Report on Patentability issued in International Application No. PCT/US2010/043240, dated Feb. 2, 2012.
International Search Report and Written Opinion issued in International Application No. PCT/US2010/043240, dated Sep. 16, 2010.
Le Bacquer et al., "Acute depletion of plasma glutamine increases leucine oxidation in prednisone-treated humans," Clin Nutr., 26(2):231-238, 2007.
Leandro eta!., "Protein misfolding in conformational disorders: rescue of folding defects and chemical chaperoning," Mini Reviews in Medicinal Chemistry, 8:901-911, 2008.
Marini et al., "Phenylbutyrate improves nitrogen disposal via an alternative pathway without eliciting an increase in protein breakdown and catabolism in control and ornithine transcarbamylase-deficient patients," The American Journal of Clinical Nutrition, 93( 6): 1248-1254, 2011.
McKeon, "MSUD Research Update," MSUD Newsletter, Maple Symp Urine Disease Family Support Group, vol. 23, No. 1, pp. 1 and 13, 2006.
Scaglia et al., "Clinical consequences of urea cycle enzyme deficiencies and potential links to arginine and nitric oxide metabolism," J Nutr, 134(10 Suppl):2775S-2782S; discussion 2796S-2797S, 2004.
Schwartz et al., "Treatment of inborn ern,>rs of metabolism," J Pediatr (Rio J), 84(4 Suppl):S8-19, 2008.
Toshima et al., "Activation ofbranched-chain alpha-ketoacid dehydrogenase complex by alpha-chloroisocaproate in normal and enzyme-deficient fibroblasts," Clin Chim Acta, 147(2):103-108, 1985.
Zhao et al., "Site-directed mutagenesis of phosphorylation sites of the branched chain a-ketoacid dehydrogenase complex," The Journal of Biological Chemistry, 269(28): 18583-18587, 1994.
Funchal et al., "Evidence That the Branched-Chain a-Keto Acids Accumulating in Maple Syrup Urin Diease Induce Morpholigical Alteration and Death in Cultured Astroxytes from Rat Ceberal Cortex", GLIA 48:230-240 (2004).
Funchal et al., "Morphological alterations and induction of oxidative stress in glial cells caused by the branched-chain a-keto acids accumulting in maple syrup urine disease", Neurochemistry International 49 640-650 (2006).
Amaral et al.; "a-Ketoisocaproic acid and leucine provoke mitochondrial bioenergetic dysfunction in rat brain", Science Direct—Brain Research 1324 75-84 (2010).
Schwartz et al., "Treatment of inborn em,>rs of metabolism," J Pediatr (Rio J), 84(4 Suppl):S8-19, 2008.
Husson et al: "Efficacy and safety of i.v. sodium benzoate in urea cycle disorders: a multicentre retrospective study", Orphanet J. Rare Dis., vol. 11, No. 1, p. 1-8.

* cited by examiner

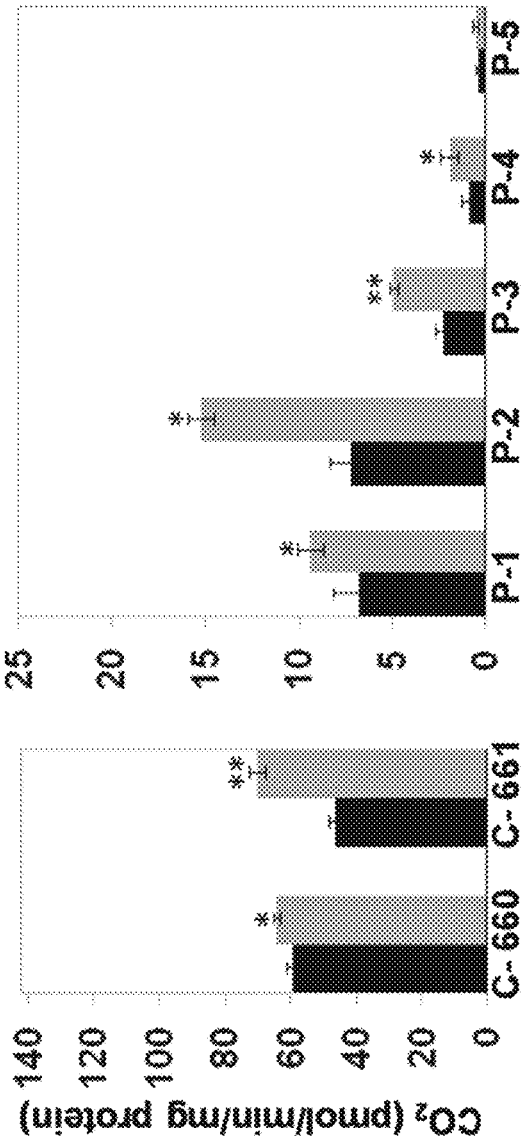
FIG. 7A
FIG. 7B
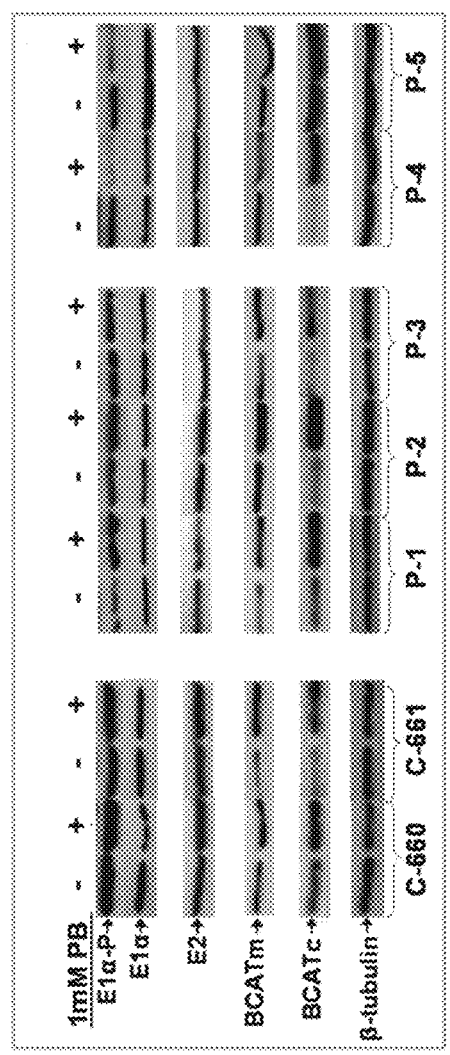
FIG. 7C

METHODS OF MODULATION OF BRANCHED CHAIN ACIDS AND USES THEREOF

CROSS-REFERENCE TO RELATED APPLICATIONS

This application is a continuation of U.S. Non-Provisional application Ser. No. 16/134,558 filed Sep. 18, 2018, which is a continuation of U.S. Non-Provisional application Ser. No. 15/653,155 filed Jul. 18, 2017, which is a continuation of U.S. Non-Provisional application Ser. No. 14/745,205 filed on Jun. 19, 2015, which is a continuation of U.S. Non-Provisional application Ser. No. 13/386,549 filed May 7, 2012, which is a national phase application under 35 U.S.C. § 371 that claims the benefit of priority from International Application No. PCT/US2010/043240 filed Jul. 26, 2010, which claims priority to U.S. Provisional Application No. 61/228,485, filed Jul. 24, 2009, all of which are incorporated herein by reference in their entirety.

BACKGROUND OF THE INVENTION

Branched chain amino acids (BCAAs) account for about 40% of the essential amino acids in healthy subjects and must be acquired through a well-balanced diet. Branched-chain amino acids are toxic in excess but are required for protein synthesis. The normal plasma levels in children for isoleucine, leucine, and valine, range from 37 to 40 µmol/L, 70 to 170 µmol/L, and 160 to 350 µmol/L, respectively. In adults, the normal plasma levels for isoleucine, leucine, and valine are 42 to 100 µmol/L, 66 to 170 µmol/L, and 150 to 310 µmol/L, respectively. The BCAAs have important physiologic functions in addition to their role as protein precursors. In peripheral tissues such as skeletal muscle, BCAAs are nitrogen donors for the synthesis of alanine and glutamine, thus moving nitrogen derived from muscle amino acid oxidation to the liver for urea synthesis. In addition, leucine acts as an anabolic nutrient signal influencing both insulin secretion by the β-cells of the pancreas and protein synthesis in skeletal muscle and some other tissues. In order to balance the body's need for BCAAs with the supply of BCAAs from the diet, the BCAA catabolic pathway is tightly regulated. The catabolic pathways of BCAAs have two common steps. The first is a reversible deamination catalyzed by vitamin-$B_6$-dependent branched-chain aminotransferase (BCATs) to produce the corresponding branched-chain α-keto acid (BCKAs). The second is the irreversible oxidative decarboxylation of the BCKAs, accomplished in a large part by control of the activity of the branched-chain α-keto acid dehydrogenase complex (BCKDC).

Deregulation of branched chain amino acid catabolism leads to an inborn error of metabolism in newborns known as maple syrup urine disease (MSUD). MSUD, also called branched-chain ketoaciduria, is an autosomal recessive disorder, typically diagnosed shortly after birth. It is caused by defects in BCKDC. The defect thus results in an accumulation of the BCAAs, namely, leucine, valine, isoleucine, and their respective α-keto acids (α-ketoisocaproate, α-ketoisovalerate, and α-keto-β-methylvalarate) in cells and body fluids. Accumulation of these three amino acids and their corresponding keto acids leads to encephalopathy and progressive neurodegeneration in untreated individuals.

The present invention addresses a long-felt need for therapies that are effective in regulating the BCAA catabolism, such as in MSUD, that can be used independently or in conjunction with dietary compliance.

SUMMARY OF THE INVENTION

In particular embodiments of the invention, there are methods and compositions for treating an individual (including a mammal, such as a human, dog, cat, horse, pig, goat, or sheep, for example) for an inborn error in amino acid metabolism with one or more ammonia scavengers. In specific aspects, the individual has a medical condition as a result of the inborn error in amino acid metabolism. Although the invention in certain cases is applicable to an inborn error in any amino acid metabolism, in specific embodiments the amino acids are branched chain amino acids. In particular cases, the individual has an inborn error in metabolism of leucine, valine, or isoleucine. In specific embodiments, the individual has MSUD, although in other embodiments the individual has hypervalinemia, isobutyryl-CoA dehydrogenase deficiency, beta-ketothiolase deficiency, 2-Methylbutyryl-CoA dehydrogenase deficiency, hypermethioninemia, homocystinuria, cystathioninuria, isovaleric acidemia, 3-Methylcrotonyl-CoA carboxylase deficiency, or 3-hydroxy-3-methylglutaryl-CoA lyase deficiency. In specific embodiments, the individual has Fragile X, tuberous sclerosis, Rett syndrome, autism, or diabetes. In some embodiments, the ammonia scavenger is one or a combination of a composition that contains or is metabolized to phenylacetate. In particular matters, the ammonia scavenger is phenylbutyrate, BUPHENYL® (sodium phenylbutyrate), AMMONAPS®, butyroyloxymethyl-4-phenylbutyrate, glyceryl tri-[4-phenylbutyrate] (HPN-100), esters, ethers, and acceptable salts, acids and derivatives thereof, for example. In specific embodiments of the invention, the composition for treatment has ammonia scavenging activity and/or has histone deacetylase inhibitor activity.

In some embodiments of the invention, there is a method of decreasing plasma levels of at least one of a branched chain amino acid or branched chain alpha-ketoacid comprising administering to an individual in need thereof a therapeutically effective amount of an ammonia scavenger compound or a pharmaceutically acceptable salt thereof, where the amount of the compound administered stimulates the baseline enzymatic activity of the branched chain dehydrogenase enzyme complex protein to levels effective in achieving target plasma levels of the branched chain amino acid or branched chain alpha-ketoacid for the individual.

Also described herein, in specific aspects, is a method of decreasing plasma levels of at least one of a branched chain amino acid or a branched chain alpha-ketoacid comprising administering to an individual in need thereof a therapeutically effective amount of at least one compound of the formula:

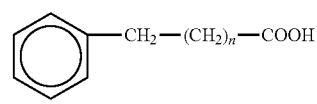

wherein n is 0, 2, 4, 6 or 8, or
a pharmaceutically acceptable salt or ester or prodrug thereof, and where the amount of the compound administered stimulates the baseline enzymatic activity of the branched chain dehydrogenase enzyme complex protein to levels effective in achieving target plasma levels of the branched chain amino acid and/or branched chain alpha-ketoacid for the individual. In an alternative embodiment, the levels of BCAA and/or BCKA are not targeted by methods of the invention.

Additionally disclosed herein, in certain embodiments, is a method for selecting, identifying or screening for a compound useful for decreasing blood plasma levels of branched chain amino acids or branched chain alpha-ketoacid, comprising the selection or identification of a compound capable of decreasing the phosphorylation of the E1α subunit of branched chain dehydrogenase enzyme protein complex at position Ser293 and Ser303; wherein the decrease in phosphorylation of the subunits at the positions is effective in increasing the enzymatic activity of the enzyme from baseline activity, in particular embodiments of the invention.

Additionally, provided in specific cases is a method of treatment for MSUD comprising administering to an individual in need thereof a therapeutically effective amount of a compound or a pharmaceutically acceptable salt or ester or prodrug thereof, wherein the amount of the compound administered is effective in dephosphorylation of the S293 and S303 residues of the E1α subunit of branched chain dehydrogenase enzyme complex protein, and the decrease in phosphorylation of the subunits at the positions is effective in increasing the enzymatic activity of the enzyme from baseline activity in the individual.

In one embodiment of the invention, there is a method of treating an individual for an inborn error of metabolism, comprising the step of administering an ammonia scavenger to the individual. In a specific embodiment, the individual has maple syrup urine disease (MSUD). In an additional specific embodiment, the ammonia scavenger compound is phenylbutyrate or a salt or ester or prodrug thereof. In some cases, the method further comprises restricting the dietary branched chain amino acid intake in said individual.

In another embodiment of the invention, there is a method of decreasing plasma levels of at least one of a branched chain amino acid or branched chain alpha-ketoacid comprising administering to an individual in need thereof a therapeutically effective amount of an ammonia scavenger compound or a pharmaceutically acceptable salt thereof; and assaying for a decrease in plasma levels of at least one of said branched chain amino acid or branched chain alpha-ketoacid. In specific aspects, the amount of the compound administered stimulates the baseline enzymatic activity of the branched chain dehydrogenase enzyme complex protein to levels effective in achieving target plasma levels of said branched chain amino acid or branched chain alpha-ketoacid for said individual. In certain cases, both branched chain amino acid and branched chain alpha-ketoacid plasma levels are decreased.

The branched chain dehydrogenase enzyme complex protein enzymatic activity is increased by at least about 5% over the baseline enzymatic activity in the individual, in particular embodiments of the invention. The individual in need thereof is an individual with an inborn error of metabolism, and in certain cases the inborn error of metabolism is MSUD, such as the types selected from the classical form, the intermediate form, the intermittent form and the thiamine-responsive form of the disease.

In specific aspects of the invention, the branched chain amino acid is at least one of leucine, isoleucine and valine. In certain cases, the branched chain alpha-ketoacid is at least one of keto-isocaproic acid, keto-methylvaleric acid, and ketoisovaleric acid. In some aspects, the ammonia scavenger compound is phenylbutyrate or a salt or ester or prodrug thereof. The salt is the sodium salt, calcium salt, lithium salt or a potassium salt, in certain cases.

In particular embodiments of the invention, phenylbutyrate or salt or ester or prodrug thereof causes decreased phosphorylation of the S293 and S303 residues of the E1 subunit of the branched chain dehydrogenase enzyme complex protein.

In one embodiment of the invention, there is a method of decreasing plasma levels of at least one of a branched chain amino acid or branched chain alpha-ketoacid comprising administering to an individual, in need thereof, a therapeutically effective amount of at least one compound of a particular formula or a pharmaceutically acceptable salt thereof, and assaying for a decrease in plasma levels of at least one of said branched chain amino acid or branched chain alpha-ketoacid. In specific embodiments, the amount of the compound administered stimulates the baseline enzymatic activity of the branched chain dehydrogenase enzyme complex protein to levels effective in achieving target plasma levels of branched chain amino acid and/or branched chain alpha-ketoacid for said individual. In specific embodiments, the compound is phenylbutyrate or a salt or ester or prodrug thereof and in further specific embodiments the phenylbutyrate or salt or ester or prodrug thereof causes decreased phosphorylation of the S293 and S303 residues of the E1 subunit of the branched chain dehydrogenase enzyme complex protein. In specific embodiments, the branched chain amino acid is at least one of leucine, isoleucine and valine and the branched chain alpha-ketoacid is at least one of keto-isocaproic acid, keto-methylvaleric acid, and ketoisovaleric acid. The compound is administered orally, intraperitoneally or intravenously, in particular aspects of the invention.

In some cases, an individual in need thereof is an individual with high plasma levels of the branched chain amino acids as compared to levels of branched chain amino acids in a healthy individual. In certain aspects, high plasma levels of branched chain amino acids are due to an inborn error of metabolism, such as MSUD, which may be selected from a group consisting of the classical form, the intermediate form, the intermittent form and the thiamine-responsive form of the disease. The method may further comprise restricting the dietary branched chain amino acid intake in said individual.

In one embodiment of the invention, there is a method for screening for a compound useful for decreasing blood plasma levels of branched chain amino acids or branched chain alpha-ketoacid, comprising selecting or identifying a compound capable of decreasing the phosphorylation of the E1 subunit of branched chain dehydrogenase enzyme protein complex at position Ser293 and Ser303; thereby increasing the enzymatic activity of said enzyme from baseline enzymatic activity. In particular embodiments, the method comprises providing the E1 subunit of branched chain dehydrogenase enzyme complex protein or a fragment thereof comprising at least 50 consecutive amino acids that include phosphorylated Ser293 and Ser303 residues or fragment thereof; contacting a candidate compound with said protein or fragment thereof; and, selecting the candidate compound that causes dephosphorylation of Ser293 and Ser303 of the E1 subunit of branched chain dehydrogenase enzyme complex. In other specific embodiments, the method comprises contacting a candidate compound with a cell expressing the E1 subunit of branched chain dehydrogenase enzyme complex protein and a branched chain amino acid dehydrogenase kinase; assessing the amount of E1 subunit phosphorylated at position S293 and S303; and, selecting the candidate compound that decreases the phosphorylation of E1 subunit of branched chain dehydrogenase enzyme complex in comparison with a control cell which has not been contacted with the candidate compound.

In certain embodiments of the invention, there is a method of treatment for MSUD comprising administering to an individual, in need thereof, a therapeutically effective amount of a compound or a pharmaceutically acceptable salt thereof, wherein the amount of said compound administered is effective in dephosphorylation of the 5293 and 5303 residues of the E1 subunit of branched chain dehydrogenase enzyme complex protein thereby increasing the enzymatic activity of said enzyme from its baseline activity in said individual. In a specific embodiment, the method further comprises restricting the dietary branched chain amino acid intake in said individual. The compound is phenylbutyrate or a salt or ester or prodrug thereof, in particular aspects. The salt is a sodium salt, a calcium salt, a lithium salt or a potassium salt, in certain cases. The compound is administered orally, intra-peritoneally or intravenously, in particular embodiments. In certain embodiments, the MSUD is selected from a group consisting of the intermediate form, intermittent form and the thiamine-responsive form of the disease.

The foregoing has outlined some of the features and technical advantages of the present invention in order that the detailed description of the invention that follows may be better understood. Additional features and advantages of the invention will be described hereinafter which form the subject of the claims of the invention.

BRIEF DESCRIPTION OF THE DRAWINGS

The foregoing and other features and aspects of the present invention will be best understood with reference to the following detailed description of a specific embodiment of the invention, when read in conjunction with the accompanying drawings, wherein:

FIGS. 7A-7C. FIGS. 7A and 7B show leucine oxidation in lymphoblast cells from control subjects (C-660, C-661) and MSUD patients (P-1, -2, -3, -4, -5) untreated or treated with 1 mM phenylbutyrate for 48 h. Leucine oxidation was measured by using radioactive assay as described in Materials and Methods and is expressed in pmol $CO_2$ released/ min/mg protein. Values are means±SD (n=3), * p≥0.05, **p≥0.01. FIG. 7C shows Western blotting of BCKD complex (E1α-phospho{P}/E1α and E2 subunits), BCATm and BCATc in lymphoblast cells from control subjects (C-660, C-661) and MSUD patients (P-1, -2, -3, -4, -5) untreated or treated with 1 mM phenylbutyrate (PB) for 48 h. β-tubulin is used as an internal control. Images are representative of three independent experiments.

FIGS. 8A and 8B show leucine oxidation in presence of CIC in lymphoblast cells from control subjects (C-660, C-661) and MSUD patients (P-1, -2, -3, -4, -5) untreated or treated with 1 mM phenylbutyrate for 48 h. Leucine oxidation was measured by using radioactive assay as described in Materials and Methods and is expressed in pmol $CO_2$ released/min/mg protein. CIC was added to all reactions in 1 mM concentration. Values are means±SD (n=3), * p≥0.05, **p≥0.01. FIG. 8C shows Western blotting of BCKD complex (E1α-phospho{P}/E1α subunit) in lymphoblast cells from control subjects (C-660, C-661) and MSUD patients (P-1, -2, -3, -4, -5) untreated or treated with 1 mM CIC or phenylbutyrate (PB) for 2 or 48 h, respectively. Images are representative of two independent experiments.

DETAILED DESCRIPTION OF THE INVENTION

Figure 1:
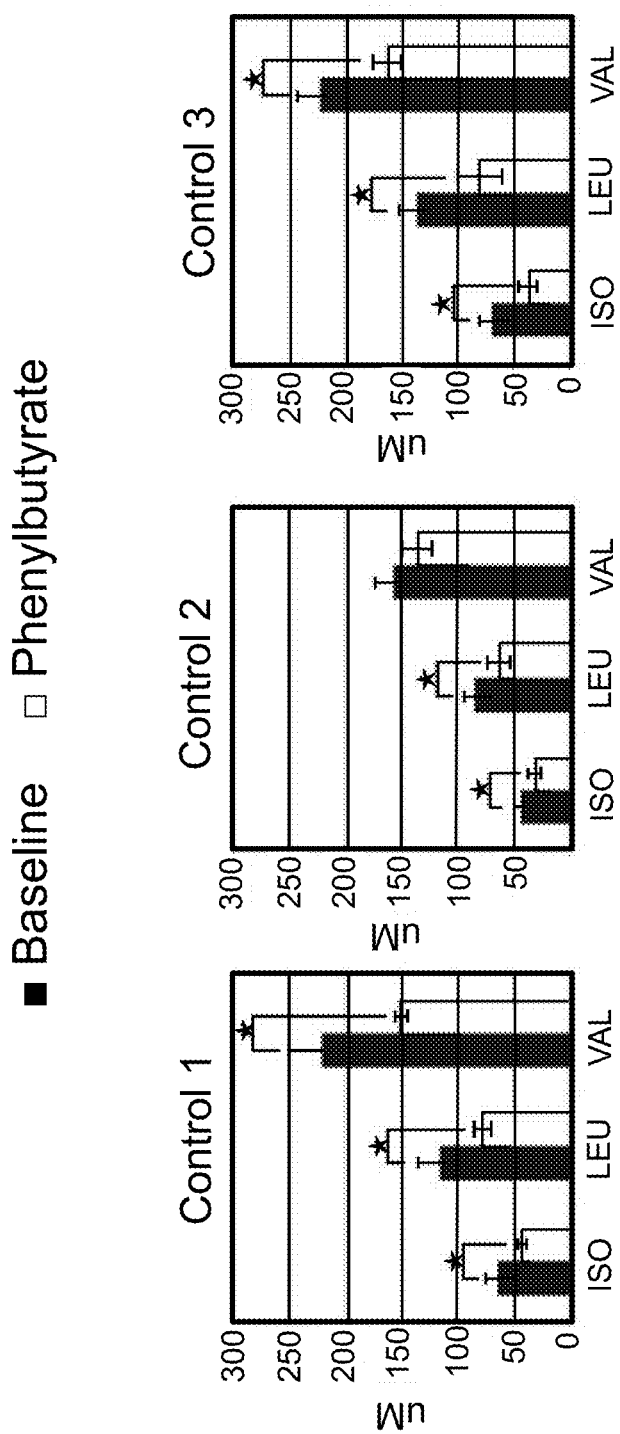
FIG. 1 is a graph representing levels of branched chain amino acids (BCAAs) in control subjects (N=3) at baseline and then after treatment with sodium phenylbutyrate (PBA). Abbreviations: Ile=Isoleucine; Leu=Leucine; Val=Valine. *: $p<0.05$. Values are average of three time points after two days of treatment. Study subjects received PBA at the dose of 10 gram/m$^2$/day divided in four equal doses every six hours for three days. The subjects received a constant protein intake of 0.6 grams/kg/day as a combination of BCAA-free formula and whole protein. Measurements were performed on day three at three different time points separated by 30 minutes in the fed state. Note that y-axis represents concentrations comparing baseline to three days of treatment. All three subjects show significantly decreased levels for all three BCAAs (leucine, isoleucine and valine) following PBA treatment.

In the following description, certain details are set forth such as specific quantities, sizes, etc. so as to provide a thorough understanding of the present embodiments disclosed herein. However, it will be obvious to those skilled in the art that the present disclosure may be practiced without such specific details. In many cases, details concerning such considerations and the like have been omitted inasmuch as such details are not necessary to obtain a complete understanding of the present disclosure and are within the skills of persons of ordinary skill in the relevant art.

I. Definitions

In keeping with long-standing patent law convention, the words "a" and "an" when used in the present specification in concert with the word comprising, including the claims, denote "one or more." Some embodiments of the invention may consist of or consist essentially of one or more elements, method steps, and/or methods of the invention. It is contemplated that any method or composition described herein can be implemented with respect to any other method or composition described herein.

As used herein, "therapeutically effective amount" refers to the amount of a compound that, when administered to a mammal for treating a state, disorder or condition, is sufficient to effect such treatment. The "therapeutically effective amount" will vary depending on the compound, the disease and its severity, and the age, weight, physical condition and responsiveness of the mammal to be treated. As used herein the term "therapeutically effective amount" refers to an amount of a compound sufficient to prevent, inhibit, reduce, or eliminate one or more causes, symptoms, or complications of elevated plasma levels of branched chain amino acids and/or branched chain alpha-ketoacid in an individual. In certain embodiments, a desired therapeutic effect is the attainment of target plasma levels of branched chain amino acid and/or branched chain alpha-ketoacid for the individual. In specific embodiments, the treatment is considered therapeutically effective when there is a particular extent of reduction in the plasma level of one or more branched chain amino acids and/or branched chain alpha-ketoacids. In certain cases, the treatment is considered therapeutically effective when there is a reduction of at least 5%, 7.5%, 10%, 12.5%, 15%, 17.5%, 20%, 22.5%, 25%, 27.5%, 30%, 32.5%, 35%, 37.5%, 40%, 42.5%, 45%, 47.5%, or 50% of the plasma level of one or more branched chain amino acids and/or branched chain alpha-ketoacids or when there is a reduction of at least about 5%, 7.5%, 10%, 12.5%, 15%, 17.5%, 20%, 22.5%, 25%, 27.5%, 30%, 32.5%, 35%, 37.5%, 40%, 42.5%, 45%, 47.5%, or 50% of the plasma level of one or more branched chain amino acids and/or branched chain alpha-ketoacids. The skilled artisan recognizes that plasma levels may be measured by standard methods in the art, for example using a plasma amino acid test or urine amino acid test by chromatography and/or mass spectrometry.

As used herein, "treating" or "treatment" of a state, disorder or condition includes: (1) preventing or delaying the appearance of clinical symptoms of the state, disorder or condition developing in a mammal that may be afflicted with or predisposed to the state, disorder or condition, but does not yet experience or display clinical or subclinical symptoms of the state, disorder or condition; (2) inhibiting the state, disorder or condition, i.e., arresting or reducing the development of the disease or at least one clinical or subclinical symptom thereof; or (3) relieving the disease, i.e., causing regression of the state, disorder or condition or at least one of its clinical or subclinical symptoms.

As used herein "ammonia scavenger drug" refers to drugs in the class with phenylacetate (PAA) that function to bind glutamine or other amino acids and result in the excretion of nitrogen. Thus, the term includes at least phenylbutyrate, phenylacetate, BUPHENYL®, AMMONUL®, AMMONAPS®, acetate, butyrate, butyroyloxymethyl-4-phenylbutyrate, glyceryl tri-(4-phenylbutyrate), esters, ethers, and acceptable salts, acids, and derivatives thereof. Salts of 4-phenylbutyric acid may be of the alkaline or earth alkaline type, e g. lithium, sodium, potassium, magnesium or calcium, for example. In specific embodiments, the ammonia scavenger drug comprises histone deacetylase inhibitor activity.

II. Maple Syrup Urine Disease

Treatment options for MSUD are extremely limited and generally constitute of dietary restriction of BCAA intake designed to maintain plasma levels within a range that is accepted to be nontoxic and supports optimal growth and development. The recommended target dietary levels of BCAA and thus the resulting plasma levels for disease management vary by age (Table 1). When prescribing diets based on "per kg body weight," ideal weight ($50^{th}$ percentile) for age is used to optimize intake. This is most important when calculating diets for patients who are failure-to-thrive. Strict dietary compliance is necessary for effective management of the disease and to prevent neurological damage.

TABLE 1

| Maple Syrup Urine Disease | 0 < 0.5 yrs | 0.5 < 1 yrs | 1 < 4 yrs | 4 < 7 yrs | 7 < 11 yrs | 11 < 19 yrs | >19 yrs |
|---|---|---|---|---|---|---|---|
| ILE, mg | 75-35/kg | 65-30/kg | 165-325/day | 225-420/day | 250-470/day | 330-570/day | 300-700/day * |
| LEU, mg | 100-50/kg | 75-35/kg | 275-535/day | 360-695/day | 410-785/day | 540-945/day | 400-1100/day |
| VAL, mg | 80-40/kg | 70-30/kg | 200-375/day | 250-500/day | 285-550/day | 375-675/day | 420-800/day * |
| Protein, g | 3.5-3.0/kg | 3.0-2.5/kg | ≥30/day | ≥35/day | ≥40/day | 50-65/day | 50-65/day |
| Energy, kcal | | | 100%-125% OF NAS/FNB RDA for age | | | | |

The human BCKDC that is defective in MSUD is encoded by six genetic loci (E1α, E1β, E2, E3, BCKD kinase and BCKD phosphatase). Based on the affected subunit of the human BCKDC, MSUD is classified into four molecular subgroups. These include types 1A, 1B, II, and III, referring to deficiencies in the E1α, E1β, E2, and the E3 subunits, respectively. A total of 166 MSUD mutations have been identified to date, with 50 in type 1A, 53 in type 1B, 49 in type 11, and 14 in type 111. BCKDC catalyzes the rate-limiting oxidative decarboxylation of the branched chain keto acids (BCKA) derived from the branched chain amino acids (BCAA), leucine, isoleucine, and valine. Mutations or deficiency in the enzyme activity results in accumulation of branched-chain 1-amino acids (BCAA) and branched chain keto acids (BCKA) that can exert neurotoxic effects. MSUD presents as a heterogeneous clinical and molecular phenotype. Severity of the disease, ranging from classical to mild variant types, is commonly classified on the basis of indirect parameters, e.g. onset, leucine tolerance and/or residual enzyme activity in cells. Long-term therapy is based on dietary restriction of BCAA intake designed to maintain plasma levels within range that is accepted to be non-toxic and supports optimal growth and development (Table 2). The daily requirement of BCAA, in face of marked deficiency of oxidative decarboxylation, is generally determined indirectly by monitoring the effect of dietary treatment on growth.

TABLE 2

| Branched Chain Amino Acid | Target Levels (µmol/L) | Normal Reference Range (µmol/L) |
|---|---|---|
| Leucine | 200-500 | 65-220 |
| Isoleucine | 100-200 | 26-100 |
| Valine | 100-300 | 90-300 |

Since there is only one dehydrogenase enzyme for all three BCAAs, all three α-keto acids accumulate and are excreted in the urine, giving it the characteristic sweet smelling odor in afflicted individuals. Such accumulation can cause a variety of symptoms including lethargy, irritability, poor feeding, abnormal movements and a characteristic odor of maple syrup in the earwax (cerumen), sweat and urine of affected individuals.

MSUD is further confirmed by detection of elevated BCKAs, by gas chromatography-mass spectroscopic, analysis of urine, and elevated BCAAs in blood by amino acid analysis. Definitive diagnosis is established by low measured activity of BCKDC in cultured lymphocytes or fibroblasts.

Severity of the disease, ranging from classical to mild variant types, is commonly classified on the basis of indirect parameters, e.g. onset of symptoms, and dietary leucine tolerance and/or residual enzyme activity in cells. There are five clinical subtypes of MSUD: the classic neonatal severe form, an intermediate form, an intermittent form, a thiamine-responsive form, and an E3-deficient form with lactic acidosis. Traditionally, the metabolic phenotype is classified as classic or intermediate on the basis of residual BCKDC activity. Rarely, affected individuals have partial BCKDC deficiency that only manifests intermittently or responds to dietary thiamine therapy. However, phenotypic distinctions are not absolute; individuals with intermediate or intermittent forms can experience severe metabolic intoxication and encephalopathy under sufficient catabolic stress. Moreover, in vitro assays of enzyme activity do not reliably predict clinical severity, age of onset, or response to potential therapies.

In classic MSUD, which is the most common form of the disorder, 50% or more of the ketoacids are derived from leucine, and the activity of BCKDC is less than 2% of normal. Affected newborns appear normal at birth, with symptoms developing between 4 to 7 days of birth. Classic MSUD phenotype include maple syrup odor evident in creumen soon after birth and in urine five to seven days of age. In untreated neonates, ketonuria, irritability, and poor feeding is observed within 48 hours of delivery. Other classic symptoms like lethargy, intermittent apnea, opisthotonus, and stereotyped movements such as "fencing" and "bicycling" are evident by four to five days of birth. If left untreated coma and central respiratory failure follow. Additionally, following the neonatal period, acute leucine intoxication (leucinosis) and neurological deterioration can develop rapidly at an age as a result of net protein degradation precipitated by infection, surgery or psychological stress. Each episode of leucinosis is associated with a high risk for cerebral edema. In older individuals, neurological symptoms vary and may include cognitive impairment, hyperactivity, anorexia, sleep disturbances, hallucinations, mood swings, focal dystonia, choreoathetosis, and ataxia. In individuals of all ages diagnosed with MSUD, nausea and vomiting are common during crisis and often necessitate hospitalization. Increased plasma concentrations of leucine and alpha-ketoisocaproic acid also lead to coma in various individuals.

Individuals with residual BCKDC activity, between 3-30% ex vivo, may appear normal during the neonatal period but nevertheless have maple syrup odor in cerumen and a consistently abnormal plasma amino acid profile. These individuals may present with feeding problems, poor growth and developmental delays as infants, or may present much later in life with nonsyndromic mental retardation. The majority of persons with intermediate MSUD are diagnosed between five months and seven years of age. Severe leucinosis, brain swelling and death can occur if individuals with intermediate MSUD are subjected to severe catabolic stress. Basic management principles for these individuals are the same as for those with classic MSUD, and the distinction between classic and intermediate type of MSUD is not absolute.

Intermittent MSUD is characterized by a normal growth and intellectual development throughout infancy and early childhood. Individuals normally can tolerate normal leucine intake. Plasma amino acid and urine organic acid profiles for these individuals are normal or show a mild elevation of BCAAs. During infection or physiological stress, these individuals develop the clinical and biochemical features of classic MSUD, and in rare cases may progress to coma leading to death. BCKDC activity is roughly 5-20% of normal.

Thiamine-responsive MSUD was described as a variant of MSUD, in which hyperaminoacidemia was completely corrected by thiamine hydrochloride with dietary restriction. The existence of individuals presenting with true thiamine-responsive MSUD is not certain. In general, such putative individuals have a residual ex vivo BCKDC activity of up to 40% normal and are not ill in the neonatal period, but present later in life with a clinical manifestation similar to intermediate MSUD. Treatment involves a combination of thiamine and dietary BCAA restriction. Hence, the in vivo contribution of thiamine is not discernable.

E3-deficient MSUD with lactic acidosis or MSUD type III, presents a combined deficiency of the branched-chain alpha-keto acid dehydrogenase, pyruvate dehydrogenase, and alpha-keto glutarate dehydrogenase complexes.

Management of MSUD includes dietary leucine restriction, high-calorie BCAA-free formulas, and frequent monitoring (Tables 1 and 2). Metabolic decompensation is corrected by treating the precipitating stress while delivering sufficient calories, insulin, free amino acids, isoleucine and valine, and in some cases hemodialysis/hemofilteration, to establish net positive protein accretion. Brain edema is a common potential complication of metabolic decompensation and requires immediate therapy in an intensive care setting. Adolescents and adults with MSUD and ADHD, depression, or anxiety respond to psychostimulants and anti-depressant medications. Orthotopic liver transplant can be an effective albeit not optimal therapy for classic MSUD. Frequent monitoring of plasma amino acid concentrations and fetal growth maybe necessary to avoid essential amino acid deficiencies during pregnancy.

III. General Embodiments of the Invention

Disorders resulting from inborn errors of metabolism (IEM) affect very small numbers of individuals, although the entire population of patients suffering the results of inherited metabolic disorders is large. Single gene defects result in abnormalities in the synthesis or catabolism of proteins, carbohydrates, or fats. Most are due to a defect in an enzyme or transport protein, which results in a block in a metabolic pathway. Effects are due to toxic accumulations of substrates before the block, intermediates from alternative metabolic pathways, defects in energy production and use caused by a deficiency of products beyond the block, or a combination of these metabolic deviations. Nearly every metabolic disease has several forms that vary in age of onset, clinical severity, and, often, mode of inheritance.

In certain embodiments of the invention, MSUD, is the result of an inborn error in metabolism that results in the accumulation of branched chain amino acids and/or branched chain alpha-ketoacids. The invention encompasses treatment of MSUD with an ammonia scavenger. In particular cases, a specific treatment regimen is employed. For example, particular dosages, formulations, schedule of administration, and so forth are utilized in the therapy of the individual.

Hence, disclosed herein is a method of decreasing plasma levels of at least one of a branched chain amino acid and/or branched chain alpha-ketoacid comprising administering to an individual, in need thereof, a therapeutically effective amount of an ammonia scavenger compound or a pharmaceutically acceptable salt thereof, where the amount of the compound administered stimulates the baseline enzymatic activity of the branched chain dehydrogenase enzyme complex protein, to levels effective in achieving target plasma levels of the branched chain amino acid and/or branched chain alpha-ketoacid, for the individual. In some embodiments, "target plasma levels" of BCAA or BCKAs are levels that achieve a therapeutic effect and are for example as defined in, but not limited to, Table 2. A therapeutic effect refers to preventing, inhibiting, reducing, or eliminating one or more causes, symptoms, or complications of elevated plasma levels of branched chain amino acids and/or branched chain alpha-ketoacid in an individual. The target plasma levels of branched chain amino acid and/or branched chain alpha-ketoacid may be varied depending on the age of the individual and the severity of the disease.

In general, the baseline enzymatic activity in MSUD individuals is about 3% to about 30% of the normal activity of the branched chain dehydrogenase enzyme protein complex. Specifically, the baseline enzymatic activity is about 5% to about 20% of the normal activity of the branched chain dehydrogenase enzyme protein complex. In an embodiment, the baseline activity is about 0% to about 40%, about 2% to about 40%, about 3% to about 30%, about 5% to about 20%, or 0% to about 2% of the normal activity of the branched chain dehydrogenase enzyme protein complex.

In specific embodiments of the invention, following administration of the therapeutic compositions of the invention, there is an increase of baseline enzymatic activity in MSUD individuals of at least 1% 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% over the level of activity prior to the treatment.

In embodiments of the individual, the individual in need thereof is an individual with an inborn error of metabolism. Specifically, the inborn error of metabolism is the MSUD. Further, the MSUD is selected from a group consisting of the intermediate form, the intermittent form or the thiamine-responsive form of the disease. In some cases, the branched chain amino acid is at least one of leucine, isoleucine and valine. Moreover, in specific embodiments the branched chain alpha-ketoacid is at least one of keto-isocaproic acid, keto-methylvaleric acid, and ketoisovaleric acid. In an embodiment, the ammonia scavenger compound is phenylbutyrate or a salt thereof. The salt is the sodium salt, calcium salt, lithium salt or a potassium salt, in specific embodiments. Specifically, the phenylbutyrate or salt thereof causes decreased phosphorylation of the S293 and S303 residues of the E1α subunit of the branched chain dehydrogenase enzyme complex protein.

Additionally, disclosed herein in some embodiments is a method of decreasing plasma levels of at least one of a branched chain amino acid or branched chain alpha-ketoacid comprising administering to an individual in need thereof a therapeutically effective amount of at least one compound of the formula:

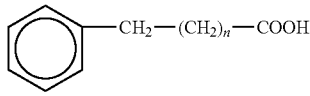

wherein n is 0, 2, 4, 6 or 8, or
a pharmaceutically acceptable salt or ester or prodrug thereof, where the amount of the compound administered stimulates the baseline enzymatic activity of the branched chain dehydrogenase enzyme complex protein to levels effective in achieving target plasma levels of branched chain amino acid and/or branched chain alpha-ketoacid for the individual.

In an embodiment, the baseline activity is about 0% to about 40%, about 2% to about 40%, about 3% to about 30%, about 5% to about 20%, or 0% to about 2% of the normal activity of the branched chain dehydrogenase enzyme protein complex. In an embodiment, the compound is phenylbutyrate or a salt thereof. In a specific embodiment, the salt is sodium salt or the calcium salt. Specifically, the phenylbutyrate or salt thereof causes decreased phosphorylation of the S293 and S303 residues of the E1 subunit of the branched chain dehydrogenase enzyme complex protein. Moreover, the branched chain amino acids are at least one of leucine, isoleucine and valine and the branched chain are at least one of keto-isocaproic acid, keto-methylvaleric acid, and ketoisovaleric acid. In some embodiments, the compound may be administered orally, intra-peritoneally or intravenously. Further, the affected individual is an individual with high plasma levels of branched chain amino acids and/or branched chain alpha-ketoacids as compared to those in a healthy individual. Specifically, the high plasma levels of branched chain amino acids and/or branched chain alpha-ketoacids are due to an inborn error of metabolism resulting in MSUD.

Further, disclosed herein is a method for screening for a compound useful for decreasing blood plasma levels of branched chain amino acids and/or branched chain alpha-ketoacid by selecting or identifying a compound capable of decreasing the phosphorylation of the E1α subunit of branched chain dehydrogenase enzyme protein complex at position Ser293 and Ser303, where the decrease in phosphorylation of the subunits at the positions is effective in increasing the enzymatic activity of the enzyme from its baseline activity. The increase in the enzymatic activity is defined as activity levels of the enzyme that are sufficient to catalyze the oxidative decarboxylation of branched chain amino acid or corresponding branched chain ketoacids, resulting in target plasma levels of the same in an individual. In certain cases, the method comprises providing the E1α subunit of branched chain dehydrogenase enzyme complex protein or a fragment thereof comprising at least 50 consecutive amino acids that include phosphorylated Ser293 and Ser303 residues or fragment thereof; contacting a candidate compound with the protein or fragment thereof; and selecting the candidate compound that causes dephosphorylation of Ser293 and Ser303 of the E1α subunit of branched chain dehydrogenase enzyme complex. Furthermore, in some aspects the method comprises contacting a candidate compound with a cell expressing the E1α subunit of branched chain dehydrogenase enzyme complex protein and a branched chain amino acid dehydrogenase kinase; assessing the amount of E1α subunit phosphorylated at position S293 and S303; and selecting the candidate compound that decreases the phosphorylation of E1α subunit of branched chain dehydrogenase enzyme complex in comparison with a control cell that has not been contacted with the candidate compound.

Additionally disclosed herein in particular cases is a method of treatment for MSUD comprising administering to an individual in need thereof a therapeutically effective amount of a compound or a pharmaceutically acceptable salt thereof, where the amount of the compound administered is effective in dephosphorylation of the S293 and S303 residues of the E1α subunit of branched chain dehydrogenase enzyme complex protein thereby increasing the enzymatic activity of the enzyme from baseline activity in the individual. Further, various methods comprise restricting the dietary branched chain amino acid intake in the individual. In general, the dephosphorylation is effective in increasing the activity of the branched chain dehydrogenase enzyme complex protein. Specifically, the compound may be phenylbutyrate or a salt thereof. The salt is the sodium salt, calcium salt, lithium salt or a potassium salt, in certain aspects. The compound is administered orally, intra-peritoneally or intravenously. In general, the individual in need thereof is an individual with high plasma levels of the branched chain amino acids and/or branched chain alpha-ketoacids as compared to levels of the respective branched chain amino acids and/or branched chain alpha-ketoacids in a healthy individual. Specifically, the individual is an individual having residual in vivo activity of the branched chain dehydrogenase enzyme complex protein. Further, the individual in need is an individual suffering from the classic form of MSUD. Alternatively, the individual is an individual with the intermediate form of MSUD. In certain cases, the individual is an individual with the intermittent form of MSUD.

IV. Pharmaceutical Preparations

Pharmaceutical preparations of the present invention are provided to treat individuals suffering from a medical condition resulting in an inborn error or metabolism. Particular pharmaceutical compositions of the present invention comprise an effective amount of one or more ammonia scavengers; in certain cases they are dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains at least one ammonia scavenger will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The ammonia scavenger may comprise different types of carriers depending on whether it is to be administered in solid, liquid or aerosol form, and whether it needs to be sterile for such routes of administration as injection, for example. The present invention can be administered intravenously, intradermally, transdermally, intrathecally, intraarterially, intraperitoneally, intranasally, intravaginally, intrarectally, topically, intramuscularly, subcutaneously, mucosally, nasally, intranasally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The ammonia scavenger may be formulated into a composition in a free base, neutral or salt form. Pharmaceutically acceptable salts include the acid addition salts, e.g., those formed with the free amino groups of a proteinaceous composition, or which are formed with inorganic acids such as, for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include an ammonia scavenger, one or more lipids, and an aqueous solvent. As used herein, the term "lipid" will be defined to include any of a broad range of substances that is characteristically insoluble in water and extractable with an organic solvent. This broad class of compounds is well known to those of skill in the art, and as the term "lipid" is used herein, it is not limited to any particular structure. Examples include compounds that contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the ammonia scavenger may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1%, 0.5%, 0.75%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of an active compound. In other embodiments, the an active compound may comprise between about 1% to about 90%, about 5% to about 90%, about 10% to about 80%, about 20% to about 75%, about 25% to about 70%, about 30% to about 65%, about 35% to about 60%, about 2% to about 75%, about 10% to about 50%, about 20% to about 40%, about 25% to about 50%, about 5% to about 20%, about 50% to about 75%, about 60% to about 80% or more of the weight of the unit, or between about 25% to about 60%, for example, and any range derivable therein. Naturally, the amount of active compound(s) in each therapeutically useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above. In certain cases, the amount that is used is at least 250 mg/kg/day, at least 275 mg/kg/day, at least 300 mg/kg/day, at least 325 mg/kg/day, at least 350 mg/kg/day, at least 375 mg/kg/day, at least 400 mg/kg/day, at least 425 mg/kg/day, at least 450 mg/kg/day, at least 475 mg/kg/day, at least 500 mg/kg/day, at least 525 mg/kg/day, at least 550, at least 575 mg/kg/day, at least 600 mg/kg/day, at least 625 mg/kg/day, at least 650 mg/kg/day, at least 675 mg/kg/day, at least 700 mg/kg/day, at least 725 mg/kg/day, at least 750 mg/kg/day, at least 775 mg/kg/day, at least 800 mg/kg/day, at least 825 mg/kg/day, at least 850 mg/kg/day, at least 875 mg/kg/day, at least 900 mg/kg/day, at least 925 mg/kg/day, at least 950 mg/kg/day, at least 975 mg/kg/day, at least 1000 mg/kg/day, at least 1.25 g/kg/day, at least 1.5 g/kg/day, at least 1.75 g/kg/day, at least 2 g/kg/day, at least 2.5 g/kg/day, at least 3 g/kg/day, at least 3.5 g/kg/day, at least 4 g/kg/day, at least 4.5 g/kg/day, at least 5 g/kg/day, at least 5.5 g/kg/day, at least 6 g/kg/day, at least 6.5 g/kg/day, at least 7 g/kg/day, at least 7.5 g/kg/day, or at least 10 g/kg/day. In specific embodiments, a dosage of 450-600 mg/kg/day is administered.

A. Alimentary Compositions and Formulations

In particular embodiments of the present invention, the ammonia scavenger is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually, for example. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792,451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration, the compositions of the present invention may alternatively be incorporated with one or more excipients in the form of a mouthwash, dentifrice, buccal tablet, oral spray, or sublingual orally-administered formulation, for example. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively, the compositions may be fashioned into a tablet or solution form that may be placed under the tongue or otherwise dissolved in the mouth.

Additional formulations that are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, or about 1% to about 2%, for example.

B. Parenteral Compositions and Formulations

In further embodiments, an ammonia scavenger may be administered via a parenteral route. As used herein, the term "parenteral" includes routes that bypass the alimentary tract. Specifically, the pharmaceutical compositions disclosed herein may be administered for example but not limited to intravenously, intradermally, intramuscularly, intraarterially, intrathecally, subcutaneous, or intraperitoneally (see U.S. Pat. Nos. 6,613,308; 5,466,468; 5,543,158; 5,641,515; and 5,399,363, for example (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof or in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

C. Miscellaneous Pharmaceutical Compositions and Formulations

In other preferred embodiments of the invention, the active compound ammonia scavenger may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

The compounds of the present invention can be used separately or in the form of mixtures, including mixtures of acids and/or salts. The compounds of the present invention may be in the forms normally employed, such as tablets, capsules, powders, syrups, solutions, suspensions and the like, and may contain flavorants, sweeteners, etc., in suitable solid or liquid carriers or diluents, or in suitable sterile media to form injectable solutions or suspensions. The active compounds of the invention will be present in such pharmaceutical compositions in the amounts sufficient to provide the desired dosage in the range as described above. Thus, for oral administration, the compounds can be combined with a suitable solid, liquid carrier or diluent to form capsules, tablets, powders, syrups, solutions, suspensions and the like. The pharmaceutical compositions, may, if desired, contain additional components such as flavorants, sweeteners, excipients and the like. For parenteral administration, the compounds can be combined with sterile aqueous or organic media to form injectable solutions or suspensions. For example, solutions in aqueous propylene glycol and the like can be used, as well as aqueous solutions of water-soluble pharmaceutically-acceptable acid addition salts or salts with base of the compounds of the present invention can be used. The injectable solutions prepared in this manner can then be administered intravenously, intraperitoneally, subcutaneously, or intramuscularly, with intramuscular administration being preferred in humans. In some embodiments, the formulation is supersaturated, include taste masking, and/or encompass liquid concentrated formulations, for example.

The compounds in accordance with the present invention may be formulated into various unit dosage forms such as tablets, soft and hard capsules, solutions and the like, by addition of pharmaceutically acceptable carriers, for example diluents such as lactose, lubricants such as magnesium stearate, binding agents such as polyvinylpyrrolidone and disintegrating agents such as calcium carboxymethyl-cellulose. Prolonged release of the active compounds in accordance with the present invention is also contemplated and is to be understood as being especially a rate of release of the active ingredient over a period of about 6 to 12 or up to 24 hours, for example.

Additionally, a dose of the pharmaceutical composition in accordance with the present invention can be appropriately determined depending upon various factors such as age and symptoms of patients, dosage forms and kinds of drugs. The size and frequency of the dosages given at any time may be varied as desired provided the indicated total daily dose is not significantly modified. Even though a unit dose of the compounds in accordance with the present invention varies depending upon various factors such as severity of disease and age of individual, it may be generally in the range of 8-13 grams/m$^2$/day mg, and preferably 10 grams/m$^2$/day. As used herein, the term "unit dose" refers to a daily dose of the compounds of the present invention for an individual which may be administered singly or as a divided dose once or several times a day. The compounds in accordance with the present invention are preferably given orally by administration of the unit dose as a single dose or divided dose once to four times a day. However, dosage amounts and frequency of administration may vary.

D. Specific Exemplary Formulations

In certain embodiments of the invention, there is a novel therapeutic use for am ammonia scavenger as an effective modulator of plasma levels of branched chain amino acids and/or branched chain alpha-ketoacids and their metabolites for the effective treatment of MSUD, and in some cases in combination with a restriction of dietary intake of branched chain amino acids and/or branched chain alpha-ketoacids, in specific cases.

In certain embodiments of the invention, there is a novel therapeutic use for sodium phenylbutyrate and its esters or prodrugs or derivatives as an effective modulator of plasma levels of branched chain amino acids and/or branched chain alpha-ketoacids and their metabolites for the effective treatment of MSUD, and in some cases in combination with a restriction of dietary intake of branched chain amino acids and/or branched chain alpha-ketoacids, in particular aspects.

In specific embodiments of the invention, the ammonia scavenger comprises phenylbutyrate (PBA) and in particular cases is used as a tablet or a powder. PBA has multiple biological activities, including its well known histone deacetylase (HDAC) inhibition activity, chemical chaperoning upon endoplasmic reticulum (ER) stress, and ammonia scavenging in urea cycle dysfunction. Sodium phenylbutyrate is a pro-drug and is rapidly metabolized to phenylacetate. Phenylacetate, a metabolically active compound, is first activated to its co-enzyme A ester, and then converted to phenylacetylCoA via beta-oxidation conjugates with glutamine via acetylation to form phenylacetylglutamine in the liver and kidneys. Phenylacetylglutamine is then excreted by the kidneys, providing an alternate vehicle for nitrogen excretion. On a molar basis, it is comparable to urea (each containing two moles of nitrogen). Therefore, phenylacetylglutamine provides an alternate vehicle for waste nitrogen excretion by increasing glutamine clearance.

In certain embodiments, the present invention discloses a novel use of the well known chemical compound phenylbutyrate, as a therapeutically effective modulator of plasma levels of branched chain amino acids and/or branched chain alpha-ketoacids and their metabolites. Without wishing to be bound by any theory, it is believed that the mechanism of BCAA depression by sodium phenylbutyrate may arise via two different possibilities. The first mechanism of PBA action may exploit its known activity as a Histone deacetylase (HDAC) inhibitor, whereby it affects the transcriptional levels of the target protein, the BCKDC. A second novel mechanism of action of PBA disclosed herein is its effects on the phosphorylation status of BCKDC, which is effective in increasing the enzymatic activity of the branched chain dehydrogenase enzyme complex protein.

Certain ammonia scavengers may be employed in the invention, including those from U.S. Patent Application Publication US2010/0008859, which is incorporated by reference herein in its entirety. In particular embodiments of the invention, Buphenyl®/Ammonaps tablets are utilized. In other embodiments of the invention, Buphenyl®/Ammonaps powder are utilized. The skilled artisan recognizes that each tablet of Buphenyl® contains 500 mg of sodium phenylbutyrate and the inactive ingredients microcrystalline cellulose NF, magnesium stearate NF, and colloidal silicon dioxide NF, and also that each gram of Buphenyl® Powder contains 0.94 grams of sodium phenylbutyrate and the inactive ingredients calcium stearate NF, and colloidal silicon dioxide NF; such a composition may be employed in the invention.

In some cases, HPN-100 is administered to the individual. In certain cases, a formulation is prepared and/or administered as described in PCT Publication WO/2008/083226 and WO 2007005633, which are incorporated herein by reference in their entirety.

In specific cases, there are preparations of high liquid dosage of an ammonia scavenger (for example, sodium 4-phenylbutyrate) in a concentrated aqueous composition, in some cases comprising at least one of a preservative and a sweetening agent, and in specific cases both, in addition to a flavoring agent. In certain embodiments, a fragrance can also be added. The supersaturated composition can have a concentration up to 500 mg/mL of sodium 4-phenylbutyrate or more, for example, such as the concentration ranges from about 300 mg/mL to about 700 mg/mL. A preservative such as sodium benzoate can be present, such as at about 2.5 mg/mL, in specific aspects. In other embodiments, the dosage can include a sweetening and/or other flavoring agent, such as about 2 mg/mL of sodium saccharine or 0.01 mg/mL of sucralose. In some embodiments a flavoring agent such as about 2 mg/mL of flavoring. This highly concentrated liquid dosage is more concentrated and more palatable, leading to easier administration to young patients and facilitating improved compliance to the dosing regimen. This concentrated solution is effective and very easy to administer to babies, because it requires only a few milliliters at any one dosing time and it is easy to administer to children because each dosage is only a few milliliters of solution at any one time.

The skilled artisan recognizes that there is a process of preparing a supersaturated composition of sodium 4-phenylbutyrate, for example, in water by adding sufficient water to a known quantity of sodium 4-phenylbutyrate at an elevated temperature of about 30° to about 800° C. to produce a concentration of about 600 mg/mL, or by adding the compound to a known quantity of water. The composition can be adjusted to a different pH, such as with an acid such as hydrochloric acid, for example. In other embodiments, there is a process for making 4-phenylbutyrate from 4-phenylbutyric acid by dissolving the same in an organic medium, treating with an inorganic alkali, heating, adding a second solvent to precipitate the product, and isolating/purifying the product.

Yet another object of this invention is to provide a process for manufacturing sodium 4-phenylbutyrate, for example, with impurities at a level less than 0.05% (weight/weight basis). The general process provided by this invention is to treat $Ph-(CHi)_2-CH(COOEt)_2$ (i.e., diethyl 2-phenylethylmalonate) with acetic acid and aqueous hydrochloric acid to produce A-phenylbutyric (or 4-phenylbutanoic) acid. In another embodiment, conversion of 4-phenylbutyric acid to its sodium salt is accomplished in an organic solvent medium with an inorganic base. In specific embodiments this invention provides a pharmaceutical liquid composition comprising a solution of sodium 4-phenylbutyrate in an aqueous medium at a concentration of at least about 300 mg/mL, including generally at a concentration of about 300 mg/mL to about 700 mg/mL, and more preferably at a concentration of about 400 mg/mL to about 600 mg/mL, for example. As a dosage the composition preferably further comprises at least one or more of a flavoring agent, including sweeteners, a preservative, and compatible mixtures thereof. The composition may also include an inorganic base.

In certain embodiments, the composition administered to the patient comprises a preservative, a flavoring agent, a fragrance, or a mixture thereof. The composition can also further comprise a preservative and a flavoring agent. The composition can also further comprise a fragrance and a sweetener as the flavoring agent.

In one embodiment, a pharmaceutical liquid composition is provided comprising sodium 4-phenylbutyrate in an aqueous medium at a concentration of at least about 300 mg/mL. In certain embodiments, the composition further comprising a preservative. The composition can also further comprise a flavoring agent. In certain embodiments, the composition comprises both a preservative and a flavor. In some embodiments, the composition comprises at least two flavoring agents and a preservative. The composition can include sodium 4-phenylbutyrate at a concentration range from about 300 mg/mL to about 700 mg/mL. The composition can also contain sodium 4-phenylbutyrate in the range from about 400 mg/mL to about 600 mg/mL. The composition can also contain the compound at a concentration of about 500 mg/mL. In certain embodiments, the weight fraction of water is less than the weight fraction of sodium 4-phenylbutyrate.

The preservative can be sodium benzoate, in certain cases. In certain embodiments, the sweetening agent is sodium saccharine. In other embodiments, the sweetening agent is sucralose. The composition can comprise a mixture of sodium saccharine and sucralose.

The composition can also further comprise a base. In certain embodiments, the base is sodium carbonate. The base can also be sodium hydroxide. The composition can further comprise 4-phenylbutyric acid. The composition can also further comprise sodium carbonate. In some embodiments, the aqueous composition does not freeze at 0° C.

Regarding sodium phenylbutyrate as an exemplary ammonia scavenger, it is known that in some cases peak plasma levels of phenylbutyrate occur within 1 hour after a single dose of 5 grams of sodium phenylbutyrate tablet with a $C_{max}$ of 218 μg/mL under fasting conditions; peak plasma levels of phenylbutyrate occur within 1 hour after a single dose of 5 grams of sodium phenylbutyrate powder with a $C_{max}$ of 195 μg/mL under fasting conditions. Buphenyl® is combined with dietary protein restriction and, in some cases, essential amino acid supplementation. Each Buphenyl® Tablet contains 62 mg of sodium (9.2% w/w) (corresponding to 124 mg of sodium per gram of sodium phenylbutyrate [12.4% w/w]) and Buphenyl® Powder contains 11.7 grams of sodium per 100 grams of powder, corresponding to 125 mg of sodium per gram of sodium phenylbutyrate (12.4% w/w).

In particular embodiments of the invention, 450-600 mg/kg/day of sodium phenylbutyrate is given in neonates, infants and children weighing less than 20 kg, and 9.9-13.0 g/m²/day is given in children weighing more than 20 kg, including adolescents and adults. The skilled artisan recognizes that one mole of sodium phenylbutyrate is metabolized to one mole of phenylacetylglutamine, and from the estimated nitrogen to be excreted on a restricted intake. Excretion of 0.09 g/kg/d of phenylacetylglutamine nitrogen would require a dose of 0.6 g/kg/d of sodium phenylbutyrate, in certain cases.

Based on pharmacokinetic data of phenylbutyrate in humans as well as in vitro kinetic studies of phenylbutyrate on the BCKD complex, a specific dosing regimen is required to achieve plasma levels sufficient for altering the phosphorylation of E1α of the BCKD complex. Based on in vitro cell, recombinant protein, and human PK analysis, at least 1 mM $C_{max}$ in plasma is required to achieve this effect. To achieve this, a dosing regimen of sodium phenylbutyrate of 10 grams/m² surface area/day divided either three times per day or more would be needed. This dosing should be modified based on the PK properties of other formulations or derivatives of phenylbutyrate.

AMMONAPS may be administered to the individual, in some cases with a protein-reduced diet. In certain cases, it is administered by mouth, through a gastrostomy, or through a nasogastric tube and, in some cases, with each meal or feeding. In certain cases, at least three hours should pass before a subsequent dose. The skilled artisan recognizes that AMMONAPS comprises sodium phenylbutyrate and that in 1 g there are 940 mg of sodium phenylbutyrate; other ingredients include calcium stearate and colloidal anhydrous silica. In order to dose accurately and especially for smaller amounts required for infants, three measuring spoons are utilized for the granules, giving doses of 0.95 g, 2.9 g and 8.6 g.

Pharmacokinetics after oral administration of phenylbutyrate have been studied in healthy volunteers (single dose of 2.5 g, n=2; single dose of 5 g, n=21), in one patient with ornithine transcarbamylase deficiency and in 8 patients with haemoglobinopathies. Phenylbutyrate is rapidly absorbed: measurable plasma levels of phenylbutyrate are detected 15 min after oral administration. Peak concentrations of approximately 1 mmol/1 are reached after 1 h. In one study, the elimination half-life was estimated to be 0.8 h. Measurable plasma levels of phenylacetate (PA) and phenylacetateglutamine (PAG) are detected 30-60 min after oral dosing of phenylbutyrate (the mean peak concentration is 45.3 and 62.8 µg/ml, respectively). The time to peak concentration increases with the dose of PB and is around 3.5 h for both metabolites after a dose of 5 g of phenylbutyrate. The elimination half-life was estimated to be 1.3 and 2.4 hours, respectively for PA and PAG. Recovery of phenylbutyrate and PAG from serial collections of urine has been evaluated in some of the cited studies. It is demonstrated that in most subjects, the kidneys within 24 h excrete approximately 80-100% of the drug as the conjugated product, PAG.

V. Nutritional Management

In certain embodiments of the invention, the individual is subject to dietary restriction in addition to utilization of the methods and compositions of the invention. To promote growth and development in infants and children, plasma levels of branched-chain amino acids and/or branched chain alpha-ketoacids are carefully monitored; levels in adults are also monitored. In individuals with MSUD, a diet with minimal levels of the amino acids leucine, isoleucine, and valine must be maintained in order to prevent neurological damage. When the condition is diagnosed, and during episodes, treatment may include eating a protein-free diet. Fluids, sugars, and possibly fats may be given through a vein (IV). Peritoneal dialysis or hemodialysis can be used to reduce the level of certain amino acids.

The health care provider will follow the levels of the branched chain amino acids and/or branched chain alpha-ketoacids closely and will adjust the diet based on the amino acid levels. Long term treatment requires a special diet, and the diet in infants may include a man-made infant formula with low levels of the amino acids leucine, isoleucine, and valine. Persons with this condition may remain on this diet permanently.

In certain embodiments of the invention, the diet of the individual with MSUD includes a variety of general factors. Intake of the branched amino acids, which are essential, must be carefully monitored. For example, the individual's tolerance of leucine must be calculated following measurement of BCAA levels and re-measured at appropriate intervals during about the first 6 to 12 months of life. The individual may intake a protein substitute that provides BCAA-free amino acids, in certain cases. In particular aspects, the individual intakes a supplement that provides necessary vitamins, minerals, and trace elements. In some cases, isoleucine, leucine, and/or valine supplements, taken as needed. In some cases the patient's levels of isoleucine and valine fall below desirable levels, or are too low in reference to the leucine level.

The individual may consume an adequate intake of calories from one or more of foods naturally low in or free from protein; specially formulated low-protein foods; and protein-free energy supplements containing glucose polymers and fats, in certain aspects of the invention.

Infants diagnosed with MSUD may be administered a special MSUD formula supplemented with controlled amounts of infant formula. Breastfeeding is beneficial to some children with MSUD but does not remove the need for the special formula. From childhood to the age of 10, the individual must continue to take a protein substitute along with other foods that are monitored to supply the correct amount of leucine. BCAA levels should be re-evaluated at least every 6-12 months. In individuals that are over the age of about 8 years old, the protein substituate may contain a certain amount of a protein equivalent (for example, 10 grams, 12 grams, 15 grams, 17 grams, or 20 grams) and may be taken as a low-volume drink. The mixture may be supplied as a powder that contains the daily requirements of amino acids, vitamins, minerals, and/or trace elements. As with children, adolescent and adult patients should have their leucine levels measured periodically.

At the recommended dose of sodium phenylbutyrate, for example, it is suggested that infants with neonatal-onset CPS and OTC deficiencies initially receive a daily dietary protein intake limited to approximately 1.6 g/kg/day for the first 4 months of life. If tolerated, the daily protein intake may be increased to 1.9 g/kg/day during this period. Protein tolerance will decrease as the growth rate decreases, requiring a reduction in dietary nitrogen intake. From 4 months to 1 year of age, it is recommended that the infant receive at least 1.4 g/kg/day, but 1.7 g/kg/day is advisable. From 1 to 3 years of age, the protein intake should not be less than 1.2 g/kg/day; 1.4 g/kg/day is advisable during this period. If caloric supplementation is indicated, a protein-free product is recommended. Caloric intake should be based upon the "Recommended Dietary Allowances", 10th ed., Food and Nutrition Board, National Research Council, National Academy of Sciences, 1989.

VI. Kits of the Invention

Any of the compositions described herein may be comprised in a kit. In a non-limiting example, an ammonia scavenger may be comprised in a kit. The kits will thus comprise, in suitable container means, an ammonia scavenger and, optionally, a diet composition with restricted branch chain amino acids of the present invention. The components of the kit may be packaged either in aqueous media or in lyophilized form. The container means of the kit will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the ammonia scavenger and any other reagent containers in close confinement for commercial sale. Such containers may include injection or blow molded plastic containers into which the desired vials are retained.

The ammonia scavenger may be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means.

VII. Examples

The following examples are presented in order to more fully illustrate the preferred embodiments of the invention. They should in no way, however, be construed as limiting the broad scope of the invention.

Example 1

Clinical Protocol

The clinical protocol was approved by the Human Subjects Institutional Review Board of the Baylor College of Medicine. The healthy control subjects and the MSUD patients were admitted into the Texas Children's Hospital General Clinical Research Center and were started on the study protocol after an informed consent was obtained. Each subject or a parent for those younger than 18 years gave written informed consent for participation in the study. Both the healthy controls (N=3) and the MSUD patients (N=5) were admitted twice in the clinical research center for 3 days each. For both admissions, the subjects received a constant protein intake of 0.6 grams/kg/day as a combination of BCAA-free formula and whole protein. On day three of admission, the patient had blood sampling at 0, 4, 6, and 8 hours during a period of frequent every two hour feeds in which ⅛th of the day's protein subscription was given. On the second admission, each subject was given sodium phenylbutyrate (Buphenyl) at a dose of 10 grams/m²/day divided into four equal doses. Otherwise, blood sampling was performed in the fed state on day 3 as in the baseline admission. Plasma samples were analyzed for amino acids and their corresponding BCKA: α-keto-β-methylvalerate (KMV), α-ketoisocaproate (KIC), and α-ketoisovalerate (KIV). The concentrations of the plasma amino acids were measured with the amino acid analyzer method. Plasma BCKA were derivatized with o-phenylenediamine and separation was made by gradient elution from a Spherisorb™ ODS2 column (250 mm×4.6 mm, 5 µm; Waters) according to protocols previously described.

PBA Treatment Causes a Decrease in the BCAA and the BCKA Levels

Figure 2:
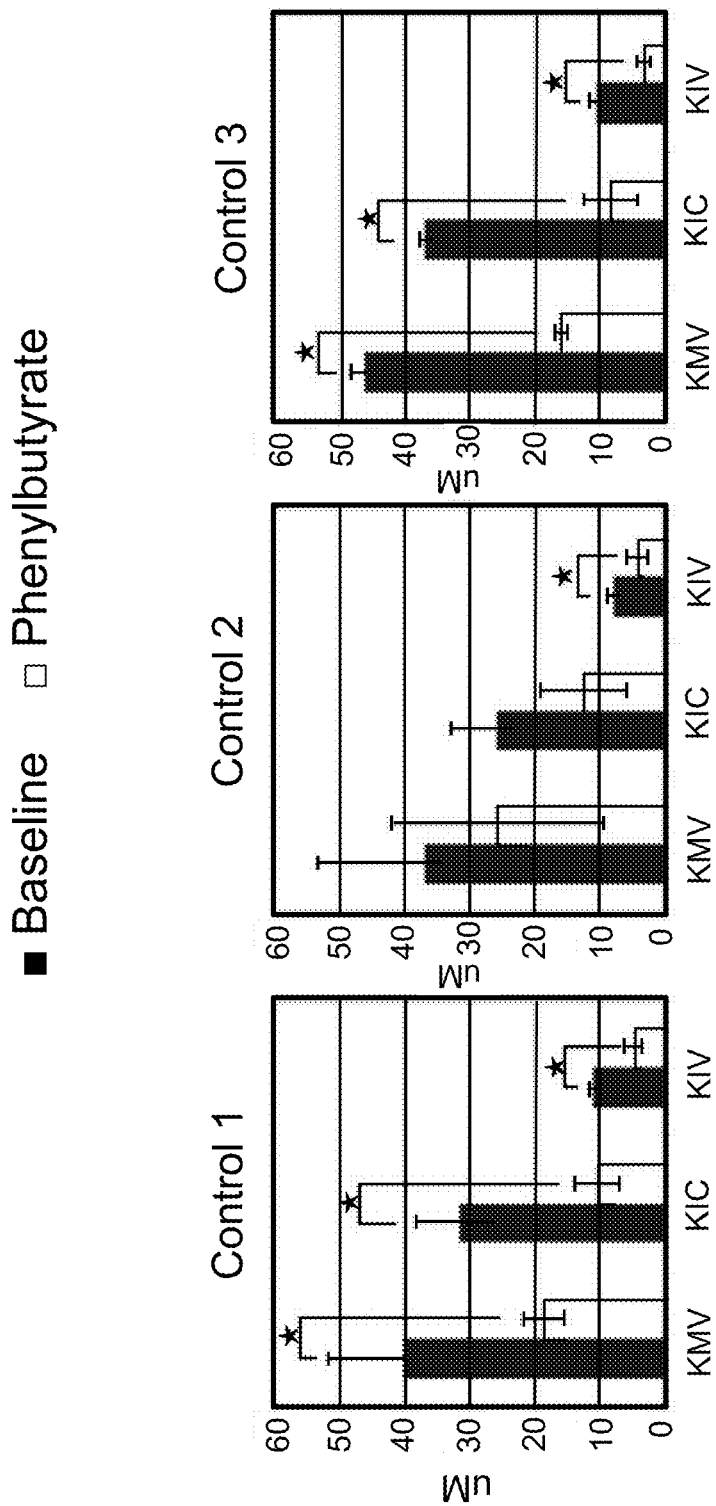
FIG. 2 is a graph representing levels of branched chain ketoacids (BCKAs) in control subjects (N=3) at baseline and then after treatment with sodium phenylbutyrate. Abbreviations: KMV=α-keto-β-methylvalerate; KIC=α-ketoisocaproate; KIV=α-ketoisovalerate. *: $p<0.05$. Values are average of three time points after two days of treatment. Subjects were all on the same steady state protein intake for three days at testing. Study subjects received PBA at the dose of 10 gram/m$^2$/day divided in four equal doses every six hours for three days. The subjects received a constant protein intake of 0.6 grams/kg/day as a combination of BCAA-free formula and whole protein. Measurements were performed on day three at three different time points separated by 30 minutes in the fed state. Note that y-axis represents concentrations comparing baseline to three days of treatment. All three subjects decreased their BCKAs.

In distinguishing the mechanism of BCAA depression by sodium phenylbutyrate, BCAA and BCKA levels were measured in control healthy subjects on a steady state protein intake, before and after sodium phenylbutyrate administration. These control subjects formed a part of a larger study comparing the efficacy of sodium phenylbutyrate vs. sodium benzoate to decrease ureagenesis. BCAA (FIG. 1) and BCKA (FIG. 2) plasma levels were found to be reduced in control subjects treated with sodium phenylbutyrate (FIGS. 1 and 2).

Figure 3:
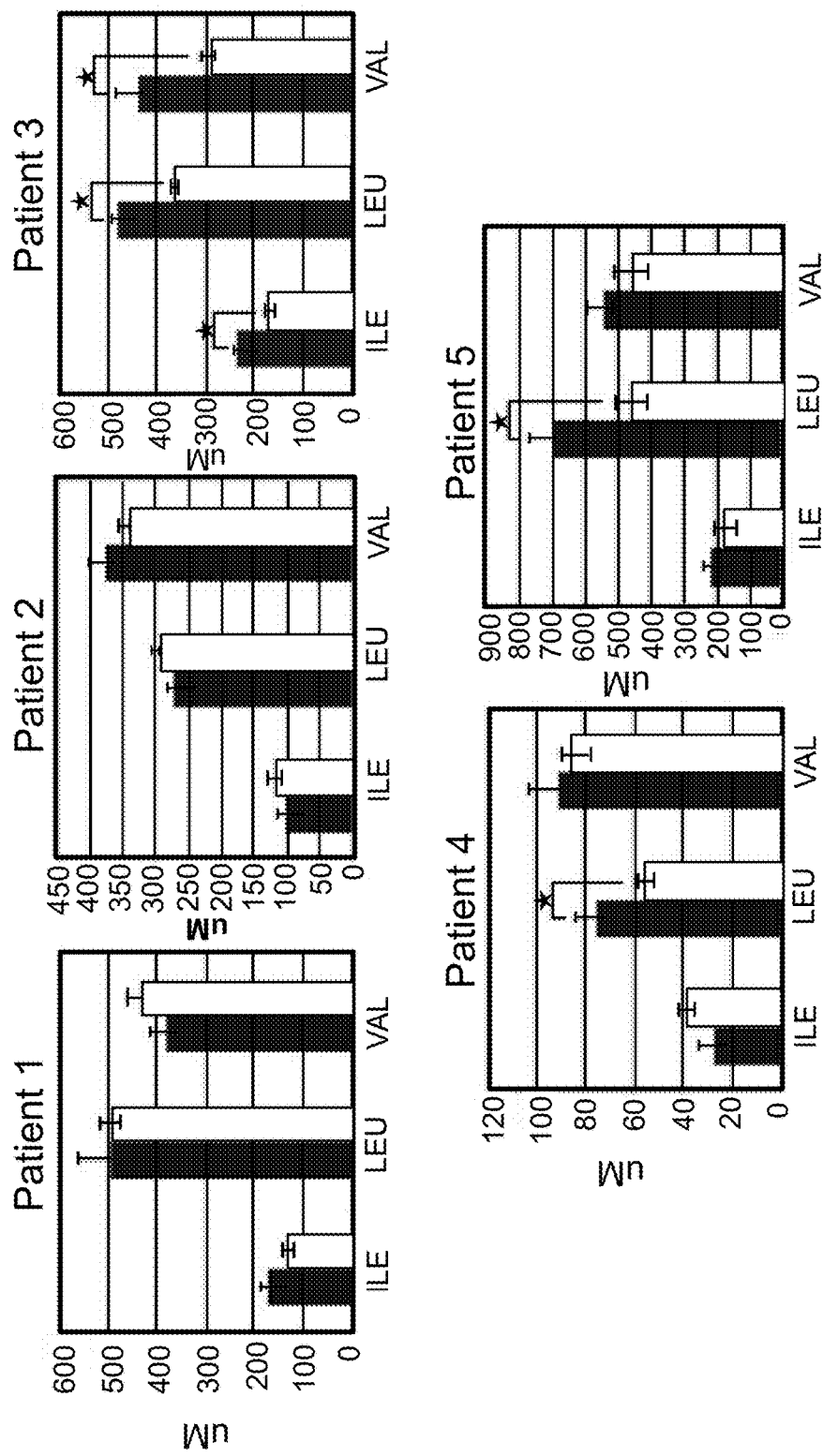
FIG. 3 is a graph representing levels of branched chain amino acids (BCAAs) in MSUD patients (N=5) at baseline and then after treatment with sodium phenylbutyrate. Values are average of three time points after two days of treatment. Patients were all on steady state protein intake for three days at testing. Study subjects received PBA at the dose of 10 gram/m$^2$/day divided in four equal doses every six hours for three days. The subjects received a constant protein intake of 0.6 grams/kg/day as a combination of BCAA-free formula and whole protein. Measurements were performed on day three at three different time points separated by 30 minutes in the fed state. Abbreviations: Ile=Isoleucine; Leu=Leucine; Val=Valine. *: $p<0.05$. Note that y-axis represents concentrations comparing baseline to three days of treatment. Three of five MSUD patients were "responders" and decreased their BCAAs.
Figure 4:
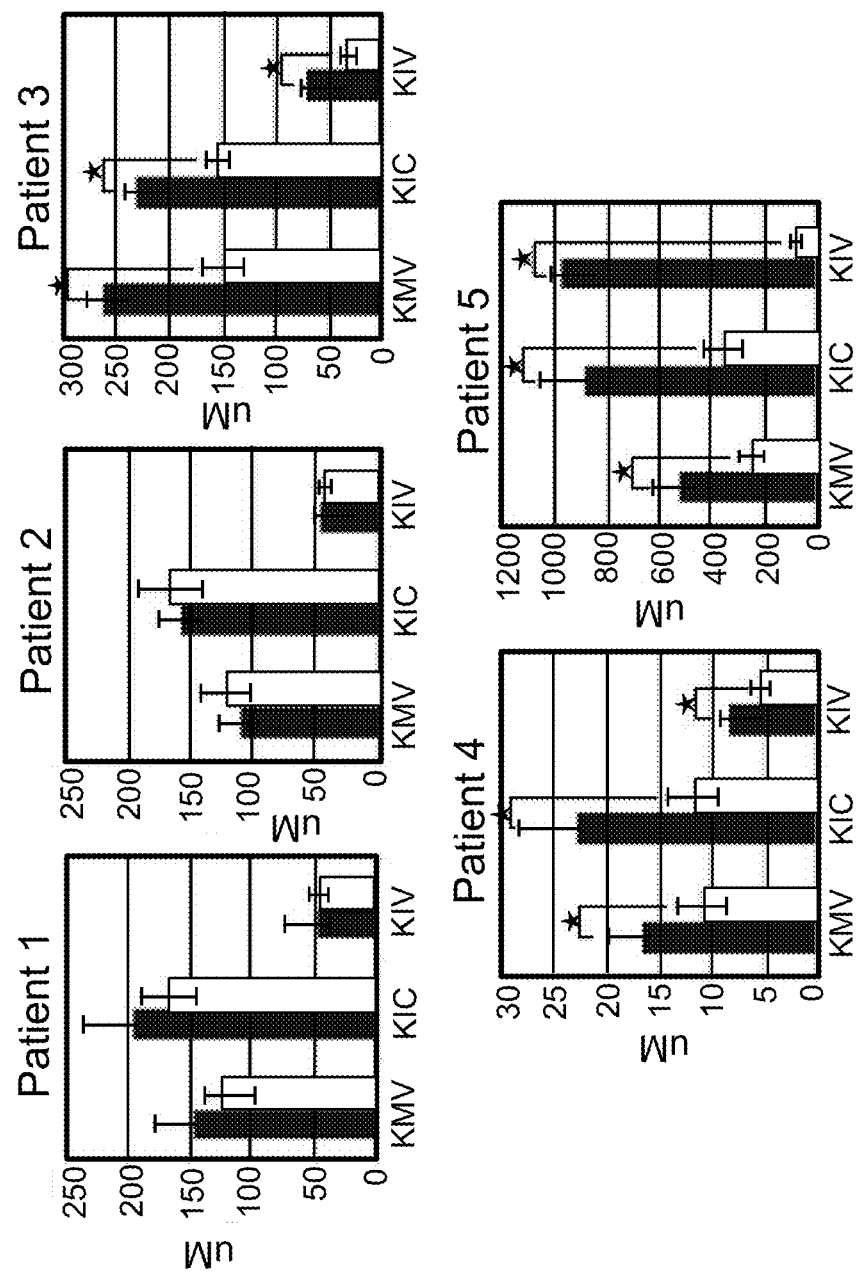
FIG. 4 is a graph representing levels of branched chain ketoacids (BCKAs) in MSUD patients (N=5) at baseline and then after treatment with sodium phenylbutyrate. Values are average of three time points after two days of treatment. Patients were all on steady state protein intake for three days at testing. The subjects received a constant protein intake of 0.6 grams/kg/day as a combination of BCAA-free formula and whole protein. Study subjects received PBA at the dose of 10 gram/m$^2$/day divided in four equal doses every six hours for three days. Measurements were performed on day three at three different time points separated by 30 minutes in the fed state. Abbreviations: KMV=α-keto-β-methylvalerate; KIC=α-ketoisocaproate; KIV=α-ketoisovalerate. *: $p<0.05$. Note that y-axis represents concentrations comparing baseline to three days of treatment. Three of five MSUD patients were "responders" and decreased their BCKAs.

Administration of PBA Correlates with Decreased Levels of BCAA and BCKA Expression in MSUD Patients To determine whether the BCAA and BCKA depression by sodium phenylbutyrate may be of therapeutic benefit in MSUD, plasma BCAA and BCKA levels were measured in MSUD subjects, on a steady state protein intake, before and after sodium phenylbutyrate administration. BCAA (FIG. 3) levels were found to be reduced and BCKA (FIG. 4) levels were found to be significantly decreased in three of five MSUD subjects treated with sodium phenylbutyrate (FIGS. 3 and 4). In the three MSUD patients, that demonstrated a decrease in plasma BCAA and BCKA levels, in response to sodium phenylbutyrate administration, leucine reduction ranged from 24% to 34% of the baseline levels. There was no clear correlation between the levels of residual activity or the mutated subunit of the BCKD complex and the biochemical response to phenylbutyrate.

Example 2

Measurement of BCKDC Expression and Activity in Patients with Intermediate and Late Onset of MSUD Five patients with intermediate and/or late onset forms of MSUD were recruited for a trial with phenylbutyrate. Patients with the intermediate form have some degree of residual enzyme activity, and, therefore, were hypothesized to have higher likelihood to respond to the treatment as compared to patients with the classic form who have no residual activity. Diagnosis of the intermediate form was made based on clinical onset of clinical symptoms beyond the neonatal period. The diagnosis of MSUD was confirmed biochemically based on the elevated leucine and on the presence of alloisoleucine in plasma. Enzyme assay and DNA analysis for BCKDC activity and genotype, respectively, on these subjects were performed and summarized (Table 3). BCKDC enzyme activity was measured on skin fibroblasts obtained from all five patients using radioactive method previously described. In this method, cultured fibroblasts cells are incubated with α-1-$^{14}$C-leucine for 4 hours in the presence of 1 mM α-chloroisocaproate in the medium to stimulate the BCKDC activity. At the end of the incubation, the amount of $^{14}CO_2$ released from leucine decarboxylation is captured onto damped filter paper. Decarboxylation activity of BCKDC is expressed as pmol of $CO_2$ released/mg protein/hour and percentage of normal activity.

DNA samples from the five patients were analyzed for mutations in the BCKDHA, BCKDHB, and DBT genes by sequencing all the coding exons and their flanking intronic regions. When only one mutation was found by sequencing, the DNA samples were further analyzed by targeted array CGH to rule out microdeletions. Interestingly, the in vitro enzyme activity did not correlate with the clinical presentation because three of the five patients have very low activity (<5%) despite the late-onset of the disease.

TABLE 3

|  | Age (years) | Gender | BCKD activity* | | % of normal control | Affected enzyme subunit | DNA analysis | |
|---|---|---|---|---|---|---|---|---|
|  |  |  | Mean ± SD | | | | Allele 1 | Allele 2 |
| Patient 1 (AG) | 24 | M | 3 ± 2.81 | | 0.96 | Pending | Pending | Pending |
| Patient 2 (JK) | 17 | M | 7.4 ± 6.7 | | 0.9 | E1α | c.887_894del | p.Y393N |
| Patient 3 (CR) | 5 | F | 2 ± 0.74 | | 0.26 | E1α | p.V412M | p.V412M |
| Patient 4 (GP) | 6 | F | 272 ± 31 | | 36.1 | E2 | c.75_76del | p.R301C |
| Patient 5 (CG) | 16 | F | 7 ± 1 | | 1.62 | E2 | p.S366P | Exon 11 del |

*pmol CO2 released/mg protein/hour

Example 3

PBA Treatment Specifically Increased BCKDC Activity

Table 4 shows the effects of Phenylbutyrate on Control and MSUD fibroblast cells. To confirm that the effect of the phenylbutyrate was specific for BCKD activity, the enzyme activity was measured in control and MSUD patient fibroblasts before and after incubation with phenylbutyrate at the concentration of 2 mM from two independent patients (one clinical responder and one clinical nonresponder) and in one control. The control fibroblast cell line showed a 1.7 fold increase in enzyme activity after incubation with phenylbutyrate. A similar increase (1.7 fold) over baseline activity was also observed in one MSUD cell line (patient 5), consistent with the biochemical response for BCAA and α-ketoacids in that patient. However, fibroblasts from Patient 3 did not show an increase of enzyme activity over baseline levels.

TABLE 4

|  | Phenylbutyrate | |
|---|---|---|
|  | − | + |
| Normal control | 100% | 176.08% |
| Patient 3 (CR) - non responder clinically | 0.59% | 0.52% |
| Patient 5 (CG) - responder clinically | 4.47% | 7.62% |

Example 4

Figure 5:
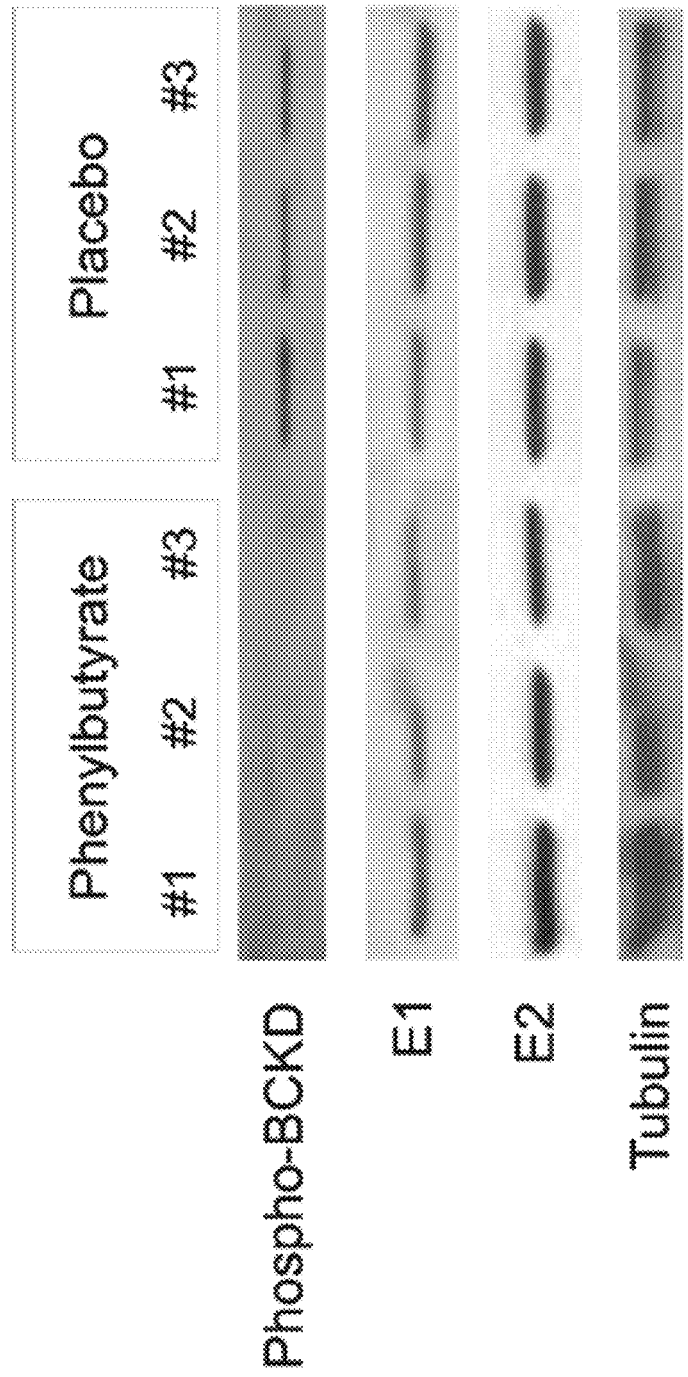
FIG. 5 is a Western blot analysis of liver extract using an antibody against the phosphorylated form of the E1 subunit of BCKDC from C57B6 mice (N=5 mice per group) treated with phenylbutyrate or placebo. To investigate the effect and mechanism of phenylbutyrate on the BCKD, mice (n=5) were treated with saline or 50 mg/kg/day of phenylbutyrate divided into three administrations for three consecutive days and after three days of treatment they were sacrificed for analyses. Proteins were extracted from mouse livers and a western blot performed using an anti-phosphoserine BCKDC antibody, the anti-BCKDC-E1 antibody, and the anti-BCKDC-E2 antibody. Each lane corresponds to the liver extract from an independent mouse (from #1 to #3). The phosphorylated form of the BCKD is significantly reduced in the phenylbutyrate treated mice as compared to the placebo group.

PBA Treatment Decreases the Phosphorylation of the E1-Alpha Subunit of the BCKDC A post-translational mechanism of regulation of the activity of BCKDC by covalent modification by phosphorylation. In order to investigate the effect and mechanism of phenylbutyrate-mediated increased activity of BCKDC, Buphenyl® or saline were given orally to C57B6 mice (N=5 mice per group) by gavage at the dose of 50 mg/kg/day divided into 3 administrations for 3 consecutive days. After three days of treatment the animals were sacrificed to harvest the liver samples. Proteins were extracted from mouse livers by homogenizing the tissue in a buffer containing 5% SDS and 0.0625 M TrisHCl. Western blot analyses were performed using an anti-Phospho BCKDC antibody (gift from Dr. Lynch), the anti-BCKDC-E1 antibody (21), and the anti-BCKDC-E2 antibody (Kamiya Biomedical Company). The Western blot analysis on the liver extract showed that the phenylbutyrate (PBA) treatment resulted in a significant reduction of the phosphorylated E1-α subunit of BCKDC as compared with the saline treated mice ($p<0.05$) (FIG. 5).

Example 5

Unaltered BCKDC Transcript Levels Following PBA Treatment

Figure 6:
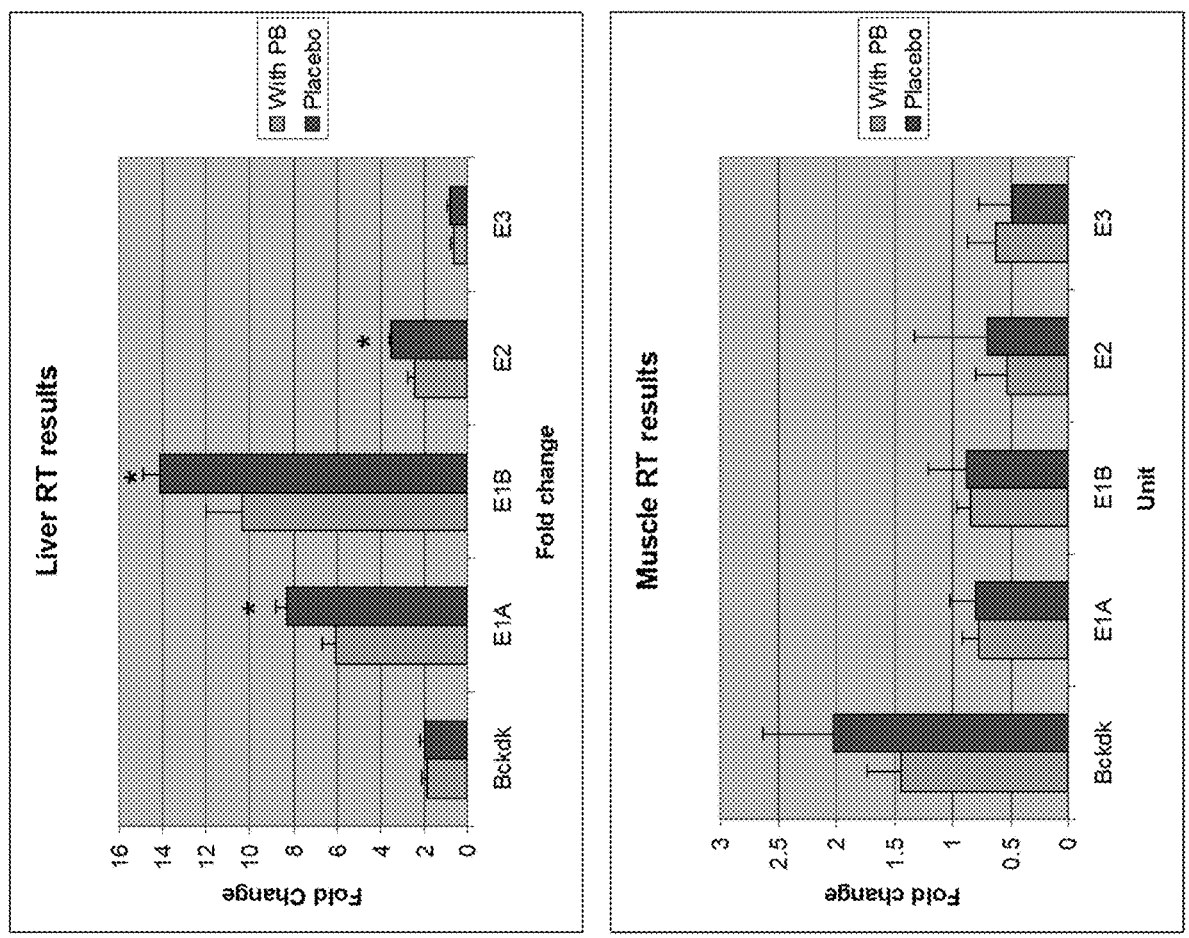
FIG. 6 shows BCKDC transcript levels, as assessed by quantitative RT-PCR, isolated from liver and muscle cells of C57B6 mice (N=5 mice per group) treated with either placebo or phenylbutyrate. The mice (n=5) were treated with saline or 50 mg/kg/day of phenylbutyrate divided into three administrations for three consecutive days and after three days of treatment they were sacrificed for analyses. The effect of phenylbutyrate is not on RNA expression of the respective BCKDC subunits.

Since PBA is a known histone deacetylase (HDAC) inhibitor, transcript levels of BCKDC were measured following treatment with PBA using quantitative RT-PCR. Five wild type mice were treated with either placebo or PBA. Following treatment the liver and muscle cells were harvested. RNA was isolated and subject to real time RT-PCR to assess the transcript levels of all the subunits of the BCKDC and regulatory kinase. The transcript levels of the E1A, E1B, E2 were found to be significantly reduced ($p<0.006$) in the liver. Hence, the observed PBA induced increased enzymatic activity of BCKDC is not due to an increase in the amount of the enzyme (since there is a decrease in transcription following PBA treatment), rather is due to the post-translational modification (decreased phosphorylation) of the existing protein. No significant changes in the transcript levels of any of the subunits of the BCKDC or in the levels of the BDK (BCDKC kinase) were observed between the placebo and the PBA treated samples (FIG. 6). Hence, PBA induced increased enzymatic activity of BCKDC is not due to the known effects of PBA as a histone deacetylase (HDAC) inhibitor.

Example 6

Phenylbutyrate Enhances E1 Activity and Inhibits E1α Phosphorylation and Inactivation.

To determine the effect of phenylbutyrate on individual BCAA catabolic enzymes, activities of mitochondrial branched chain amino transferase (BCATm) and BCKDC enzymes were measured with and without phenylbutyrate using purified recombinant enzymes. BCATm generates the BCKA products that are elevated in MSUD and are the substrates for BCKDC. BCATm activity was measured at pH 8.0 and 298 K as described in Example 2. Kinetics of the E1 decarboxylase reaction with and without phenylbutyrate were determined in the presence of an artificial electron acceptor 2, 6-dichlorophenolindophenol (DCPIP). The assay mixture contained 100 mM potassium phosphate, pH 7.5, 2.0 mM $MgCl_2$, 0.2 mM thiamin diphosphate (ThDP) and 0.1 mM DCPIP. The rate of decarboxylation at 30° C. was measured by monitoring the reduction of the dye at 600 nm (24, 25). For the overall BCKDC activity assay, the enzymes were exchanged into phosphate buffer (30 mM potassium phosphate, pH 7.5) containing 5 mM DTT using a PD-10 column and the enzyme concentrations were calculated from the absorption maxima at 280 nm. The protein complex was reconstituted with E1, lipoylated E2 (lip-E2) and E3 at a molar ratio of 12:1:55, in which lip-E2 exists as a 24-mer. The assay mixture contained 30 mM potassium phosphate pH 7.5, 100 mM NaCl, 3 mM NAD⁺, 0.4 mM CoA, 2 mM MgCl$_2$, 2 mM DTT, 0.1% Triton X-100, and 2 mM ThDP. The overall reaction was monitored by formation of NADH at 340 nm. The apparent rate constants ($k_{app}$) at different substrate concentrations for all of the above assays were determined from the absorption changes at the individual wavelength maximum. The $k_{app}$ rate constants were fit using the following equation:

$$k_{app} = k_{cat}[S]/(K_m + [S])$$

The phosphorylation of E1 was carried out in the phosphorylation reaction mix (30 mM HEPES, pH 7.4, 2 mM DTT, 1.5 mM MgCl2, and 0.2 mM EGTA) with and without addition of phenylbutyrate. E1, E2, and E3 proteins were mixed at 12:1:55 molar ratio in a 0.1 ml reaction mix, and 0.1 µg of maltose-binding protein-tagged rat BCKDC kinase (BDK) was added. The mix was pre-incubated at room temperature for 15 minutes. The phosphorylation reaction was started after addition of 0.4 mM ATP to the reaction mix, and the reaction was terminated at different time points by addition of higher salt concentration. Overall BCKDC activity was measured as described above.

As shown in Table 5, there was no effect of phenylbutyrate on BCATm kinetics including $k_{cat}$ and $K_m$. BCKDC has multiple enzyme activities and therefore, we tested the following enzyme activities in the presence and absence of phenylbutyrate: E1 decarboxylase—both unphosphorylated (fully active) and completely phosphorylated (inactive) E1, ability of BCKDC kinase to phosphorylate and inactivate E1, and overall BCKDC activity. As shown in Table 6, phenylbutyrate enhanced unphosphorylated E1 (fully active enzyme) catalyzed decarboxylation of all three BCKA significantly. It not only increased the $k_{cat}$ but also increased the sensitivity of the enzyme to BCKA by lowering their $K_m$ values. Phenylbutyrate did not have an effect on phosphorylated E1 (inactive enzyme), but did prevent completely phosphorylation and inactivation of E1 in the presence of BCKDC kinase (Table 5, compare $k_{cat}$ and $K_m$ values for phosphorylated E1 and E1 plus phenylbutyrate and BDK). Phenylbutyrate enhanced overall BCKDC activity as shown by the increases of 50% to 70% in $k_{cat}$ values for BCKAs (Table 6). Therefore, phenylbutyrate appears to activate decarboxylase activity and increase the activity state of BCKDC by blocking kinase catalyzed inactivation of E1.

TABLE 5

Phenylbutyrate protected E1 from BDK induced inactivation and had no effect on the activity of phosphorylated E1[a].

| | $k_{cat}$ (min⁻¹) | | | $K_m$ (µM) | | |
|---|---|---|---|---|---|---|
| Additions | KIC | KMV | KIV | KIC | KMV | KIV |
| | E1 catalyzed decarboxylase activity | | | | | |
| [−] Phenylbutyrate | 7.6 ± 1.0 | 5.2 ± 0.8 | 12.0 ± 1.2 | 39.0 ± 2.0 | 45.0 ± 4.0 | 48.0 ± 3.0 |
| [+] Phenylbutyrate | 20.2 ± 1.5 | 18.0 ± 1.0 | 25.0 ± 2.0 | 24.0 ± 2.0 | 21.0 ± 3.0 | 22.0 ± 2.0 |
| [+] Phenylbutyrate[b] [−] BDK | 19.8 ± 1.7 | 20.0 ± 1.1 | 28.0 ± 1.9 | 27.0 ± 2.0 | 18.0 ± 2.0 | 20.0 ± 3.0 |
| [+] Phehylbutyrate[b] [+] BDK | 20.6 ± 2.5 | 22.0 ± 1.8 | 26.0 ± 2.2 | 21.0 ± 1.9 | 21.0 ± 3.0 | 25.0 ± 2.0 |
| | E1 catalyzed decarboxylase activity measured after inactivation by BDK[b] | | | | | |
| [−] Phenylbutyrate | 0.9 ± 0.1 | 0.6 ± 0.1 | 0.5 ± 0.1 | 532.0 ± 35.0 | 610.0 ± 28.0 | 680.0 ± 20.0 |
| [+] Phenylbutyrate | 0.9 ± 0.1 | 0.6 ± 0.1 | 0.6 ± 0.1 | 550.0 ± 27.0 | 642.0 ± 38.0 | 720.0 ± 47.0 |

[a]E1 protein was reconstituted with phenylbutyrate (1.0 mM) first and then BCKD kinase (BDK) (0.1-0.5 µg) and ATP (0.4-1.0 mM) were added.
[b]E1 protein was phosphorylated first with the addition of BDK (0.1 µg) and ATP (0.4 mM).
Abbreviations:
KMV, α-keto-β-methylvalerate;
KIC, α-ketoisocaproate;
KIV, α-ketoisovalerate.

TABLE 6

Phenylbutyrate enhanced overall BCKDC activity[a].

| | Activity of BCKDC[b] | | | | | |
|---|---|---|---|---|---|---|
| | $k_{cat}$ (min⁻¹) | | | $K_m$ (µM) | | |
| Additions | KIC | KMV | KIV | KIC | KMV | KIV |
| [−] Phenylbutyrate | 140.0 ± 15.0 | 118.0 ± 10.0 | 197.0 ± 12.0 | 45.0 ± 6.0 | 53.0 ± 7.0 | 55.0 ± 4.0 |
| [+] Phenylbutyrate | 255.0 ± 10.0 | 226.0 ± 18.0 | 309.0 ± 15.0 | 41.0 ± 5.0 | 50.0 ± 3.0 | 40.0 ± 5.0 |

Abbreviations:
KMV, α-keto-β-methylvalerate;
KIC, α-ketoisocaproate;
KIV, α-ketoisovalerate.

Thus, the present invention provides a novel mechanism of action of PBA for the regulation of BCKDC enzymatic activity that affects the post-translational modification of this protein complex, namely dephosphorylation, thereby increasing its enzymatic activity. The increased enzymatic activity of BCKDC thus obtained is effective in treatment of diseases related to the defective catabolism of branched chain amino acids.

For example, the global action of phenylbutyrate and its derivatives on global phosphorylation may be applied to the treatment of diseases where phosphorylation status of target proteins are regulated by phosphorylation wherein alteration of phosphorylation status of the protein may lead to either decrease or increase in enzymatic activity. This alteration of enzymatic activity would translate into therapeutically beneficial endpoints in the associated disease process.

E2 mutations (Table 7), activation of enzyme activity results from inhibition of phosphorylation state of E1α, in specific embodiments of the invention. In the other patient cell lines, enhanced activity did not appear to correlate with phosphorylation changes but was rather related with increased levels of the BCAT isozymes.

TABLE 7

Characteristics of the MSUD patients.

| | Age (years) | Gender | Fibroblast BCKDC activity[a] Mean ± SD | Fibroblast BCKDC activity[a] % of normal control | Lymphoblast BCKDC activity[a] Mean ± SD | Lymphoblast BCKDC activity[a] % of normal control | Affected enzyme subunit | DNA analysis Allele 1[b] | DNA analysis Allele 2[b] |
|---|---|---|---|---|---|---|---|---|---|
| Patient 1 | 24 | Male | 3 ± 2.81 | 0.96 | 463.6 ± 32.1 | 9.13 | E1α | p.G290R (p.G245R)[c] | p.G290R (p.G245R)[c] |
| Patient 2 | 17 | Male | 7.4 ± 6.7 | 0.9 | 560.6 ± 98.8 | 11.04 | E1α | c.887_894del[d] | p.Y438N (p.Y393N)[d] |
| Patient 3 | 5 | Female | 2 ± 0.74 | 0.26 | 689.9 ± 72 | 13.59 | E1α | p.V412M (p.V367M)[e] | p.V412M (p.V367M)[e] |
| Patient 4 | 6 | Female | 272 ± 31 | 36.1 | 157.1 ± 100.7 | 3.09 | E2 | c.75_76del[f] | p.R301C (p.R240C)[g] |
| Patient 5 | 16 | Female | 7 ± 1 | 1.62 | 73.7 ± 18.1 | 1.45 | E2 | p.S366P (p.S305P)[g] | Exon 11 del[g] |

[a]Enzyme activity measured on fibroblasts or lymphoblasts is expressed in pmol $CO_2$ released/mg protein/hour.
[b]The numbering systems of amino acid residues beginning with the initiation Methionine as +1 or with the amino terminus (in parenthesis) are both listed.
[c]This mutation was previously reported in homozygous state by Chuang et al. (1995) in patients with an intermediate form of MSUD.
[d]Mutations previously reported by Zhang et al. (1989) and Chuang et al. (1995) in a patient with classic MSUD.
[e]Mutations previously reported by Henneke et al. (2003) in patient with classic MSUD.
[f]Mutation previously reported by Fisher et al. (1993) in compound heterozygous state with the p.E163X mutation in a patient with classic MSUD.
[g]Mutations not previously reported.

Example 7

Enzyme Activity in Control and Patient Lymphoblast Cell Lines.

Following treatment with phenylbutyrate, enzyme activity in control and patients' lymphoblast cell lines was measured. Transformed lymphoblast cell lines were available from all 5 MSUD patients and from 2 controls to measure BCKDC activity. Lymphoblasts were incubated for 48 h with and without 1 mM phenylbutyrate (a lower concentration of phenylbutyrate was used because of higher sensitivity of these cells as compared to fibroblasts to the drug) then BCKDC activity was measured without α-chloroisocaproate addition (CIC). As shown in FIG. 3, culturing lymphoblasts from controls with phenylbutyrate significantly enhanced leucine oxidation in both control (FIG. 7A) and patient lymphoblasts (FIG. 7B), with the exception of patient 5 in which the increase was not significant. Western blotting (FIG. 7C) with antibodies that detect E1α, E1α-P, E2, and the BCAT isozymes revealed a complex effect of phenylbutyrate. Of the 3 patient responders, lymphoblasts from patients 4 and 5 exhibited a decrease in the phosphorylation state of E1α with no apparent change in E1 levels. Neither the controls nor patients 1, 2 and 3 responded. Phenylbutyrate also appeared to influence the levels of the BCAT isozymes, particularly the cytosolic isozyme BCATc which was expressed in lymphoblasts and appeared to increase in response to phenylbutyrate in all of the lymphoblasts but patient 5 lymphoblast cells. The levels of the mitochondrial isozyme, BCATm, were slightly elevated in both controls as well as patients 1 through 3 upon phenylbutyrate treatment. Thus, in cells from the two patients with Example 8

Figure 8A:
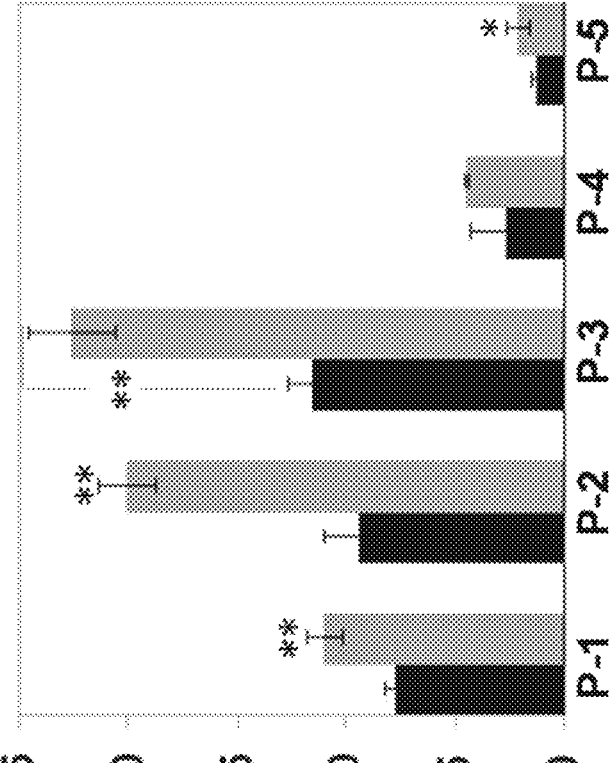
FIGS. 8A-8C.
Figure 8B:
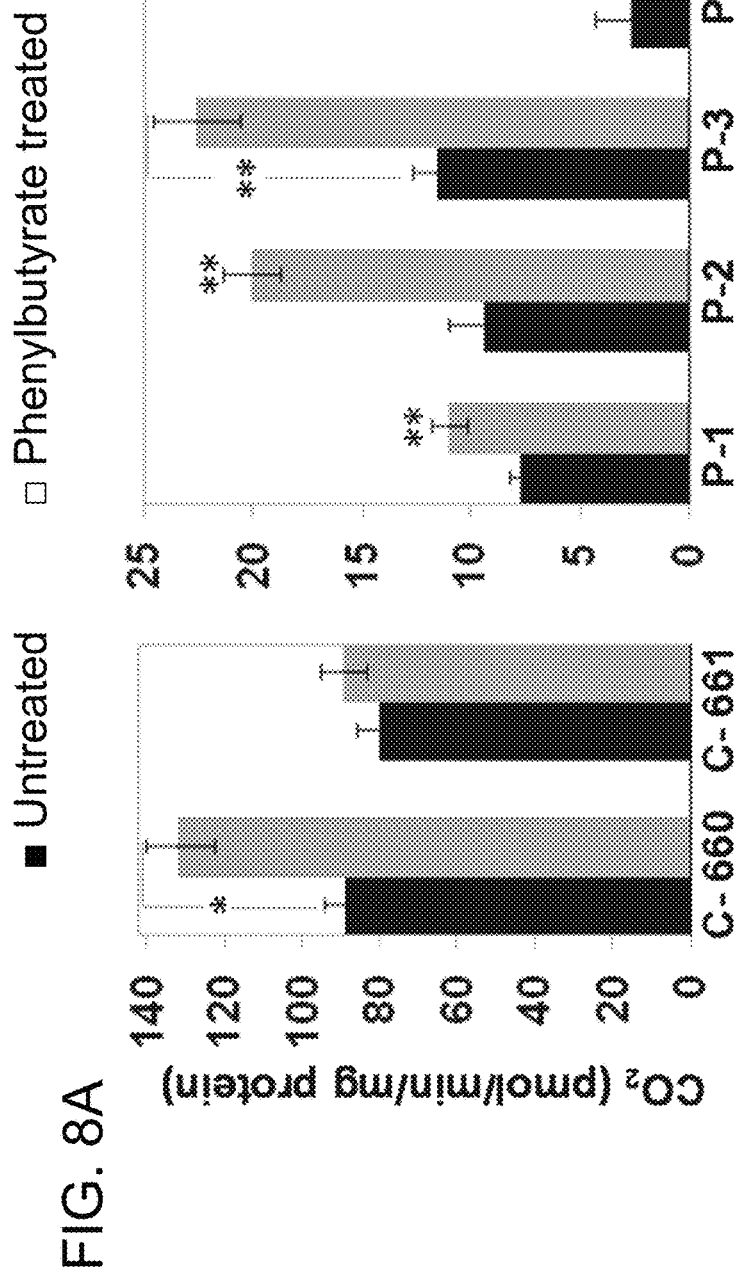
Figure 8C:
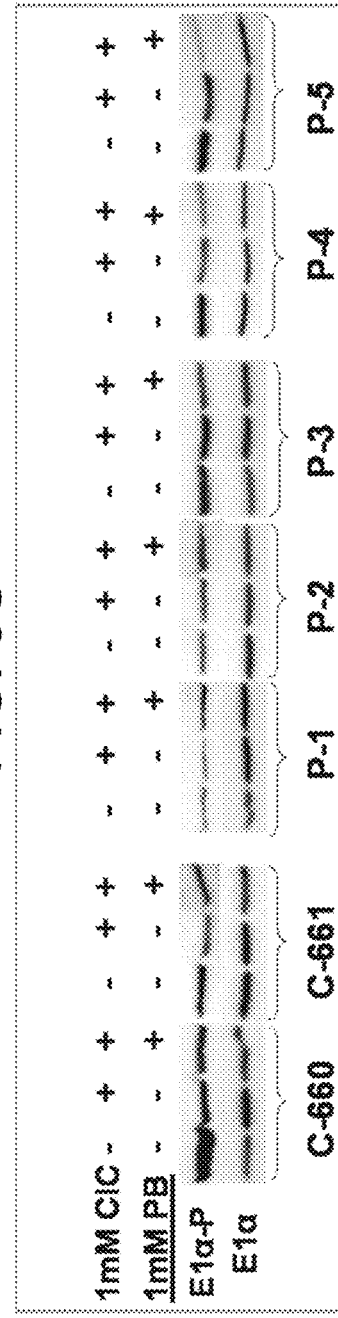

Phenylbutyrate Enhancement of BCAA Oxidation Involves Both Effects on Phosphorylation State of E1 and a Direct Action on Enzyme Activity Alpha-chloroisocaproate (CIC) is a known inhibitor of branched-chain alpha-keto acid dehydrogenase kinase (BDK) (Harris et al., 1982) and is added routinely when assaying BCKDC activity in human cell lines. Because phenylbutyrate affects E1α phosphorylation state in vivo (see FIG. 5), leucine oxidation was measured in the same cell lines as in FIG. 8 with CIC in the assay. Both control cells exhibited higher activity in the presence of CIC than alone and oxidation was increased by phenylbutyrate (FIGS. 8A and 8B). In the patient samples, patients 1 and 2 showed a similar pattern of response to phenylbutyrate as observed in the absence of CIC. On the other hand, in patient 3 lymphoblast leucine oxidation was higher than in the other cell lines and rates nearly doubled in the cells incubated with phenylbutyrate. Western blotting (FIG. 8C) with antibodies that detect E1α and E1α-P showed that CIC alone, or together with phenylbutyrate, decreases the phosphorylation state of E1α in both controls and patients 4 and 5 but has no effect on patients 1, 2, and 3. CIC did not have any effect on E2 or the BCAT isozyme levels. Taken together, the results indicate that the ability of phenylbutyrate to enhance BCAA oxidation involved both effects on phosphorylation state of E1 and a direct action on enzyme activity. Changes in BCAT isoenzyme activity also impacts BCKA production, in specific cases. All patient cell lines accumulated more KIC than observed in control cell lines.

REFERENCES

All patents and publications mentioned in this specification are indicative of the level of those skilled in the art to which the invention pertains. All patents and publications herein are incorporated by reference to the same extent as if each individual publication was specifically and individually indicated to be incorporated by reference in their entirety.

Patents and Patent Applications

U.S. Patent Application Publication US2010/0008859
PCT Publication WO/2008/083226
U.S. Pat. No. 6,613,308
U.S. Pat. No. 5,641,515
U.S. Pat. No. 5,580,579
U.S. Pat. No. 5,792,451
U.S. Pat. No. 5,466,468
U.S. Pat. No. 5,543,158
U.S. Pat. No. 5,641,515
U.S. Pat. No. 5,399,363
U.S. Pat. No. 5,629,001

Publications

Chuang, J. L., J. R. Davie, J. M. Chinsky, R. M. Wynn, R. P. Cox, and D. T. Chuang. Molecular and biochemical basis of intermediate maple syrup urine disease. Occurrence of homozygous G245R and F364C mutations at the E1 alpha locus of Hispanic-Mexican patients. J Clin Invest 95:954-63 (1995).

Fisher, C. W., C. R. Fisher, J. L. Chuang, K. S. Lau, D. T. Chuang, and R. P. Cox. Occurrence of a 2-bp (AT) deletion allele and a nonsense (G-to-T) mutant allele at the E2 (DBT) locus of six patients with maple syrup urine disease: multiple-exon skipping as a secondary effect of the mutations. Am J Hum Genet 52:414-24 (1993).

Harris, R. A., R. Paxton, and A. A. DePaoli-Roach. Inhibition of branched chain alpha-ketoacid dehydrogenase kinase activity by alpha-chloroisocaproate. J Biol Chem 257:13915-8 (1982).

Henneke, M., N. Flaschker, C. Helbling, M. Muller, P. Schadewaldt, J. Gartner, and U. Wendel. Identification of twelve novel mutations in patients with classic and variant forms of maple syrup urine disease. Hum Mutat 22:417 (2003).

Recommended Dietary Allowances", 10th ed., Food and Nutrition Board, National Academy of Sciences, 1989

Remington's Pharmaceutical Sciences, 18th Ed. Mack Printing Company, 1990.

Zhang, B., H. J. Edenberg, D. W. Crabb, and R. A. Harris. Evidence for both a regulatory mutation and a structural mutation in a family with maple syrup urine disease. J Clin Invest 83:1425-9 (1989).

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method of treating an individual having a metabolic disorder from an inborn error in metabolism of one or more branched chain amino acids, comprising administering to the individual a therapeutically effective amount of a composition comprising phenylbutyrate, butyroyloxymethyl-4-phenylbutyrate, glyceryl tri-[4-phenylbutyrate] (HPN-100), esters thereof, ethers thereof, salts thereof, or a combination thereof, wherein the metabolic disorder is selected from the group consisting of hypervalinemia, isobutyryl-CoA dehydrogenase deficiency, beta-ketothiolase deficiency, 2-Methylbutyryl-CoA dehydrogenase deficiency, hypermethioninemia, homocystinuria, cystathioninuria, isovaleric acidemia, 3-Methylcrotonyl-CoA carboxylase deficiency, or 3-hydroxy-3-methylglutaryl-CoA lyase deficiency, and a combination thereof.

2. The method of claim 1, wherein the metabolic disorder comprises an increase in blood plasma levels of branched chain amino acids and/or branched chain alpha-keto acids.

3. The method of claim 2, wherein the branched chain amino acid is at least one of leucine, isoleucine, and valine.

4. The method of claim 2, wherein the branched chain alpha-keto acid is at least one of keto-isocaproic acid, keto-methylvaleric acid, and ketoisovaleric acid.

5. The method of claim 1, wherein the salt of phenylbutyrate is sodium phenylbutyrate.

6. The method of claim 1, wherein the salt is the sodium salt, calcium salt, lithium salt, potassium salt, or a mixture thereof.

7. The method of claim 1, wherein the administration of the composition results in a decrease in blood plasma levels of branched chain amino acids and/or branched chain alpha-keto acids.

8. The method of claim 1, wherein administration of the composition stimulates the baseline enzymatic activity of the branched chain dehydrogenase enzyme complex protein to levels effective in achieving decreased branched chain amino acid and/or branched chain alpha-keto acid levels.

9. The method of claim 1, further comprising assaying for a decrease in plasma levels of at least one of said branched chain amino acids and/or assaying for a decrease in plasma levels of branched chain alpha-keto acids.

10. The method of claim 1, wherein the metabolic disorder is isovaleric academia.

* * * * *